United States Patent
Reaungamornrat et al.

(10) Patent No.: US 12,373,963 B2
(45) Date of Patent: Jul. 29, 2025

(54) UNSUPERVISED MULTITASK ENSEMBLE FOR SPATIAL TRANSFER OF MULTI-STRUCTURES VIA PARTIAL POINT CLOUD MATCHING

(71) Applicant: Siemens Healthineers AG, Forchheim (DE)

(72) Inventors: Sureerat Reaungamornrat, Havertown, PA (US); Florin-Cristian Ghesu, Baiersdorf (DE)

(73) Assignee: Siemens Healthineers AG, Forchheim (DE)

( * ) Notice: Subject to any disclaimer, the term of this patent is extended or adjusted under 35 U.S.C. 154(b) by 485 days.

(21) Appl. No.: 17/930,344

(22) Filed: Sep. 7, 2022

(65) Prior Publication Data

US 2024/0078690 A1  Mar. 7, 2024

(51) Int. Cl.
G06T 7/00 (2017.01)
G06T 7/33 (2017.01)
G16H 30/20 (2018.01)
G16H 30/40 (2018.01)

(52) U.S. Cl.
CPC ............ G06T 7/337 (2017.01); G16H 30/20 (2018.01); G16H 30/40 (2018.01); G06T 2207/10028 (2013.01); G06T 2207/20081 (2013.01); G06T 2207/20084 (2013.01)

(58) Field of Classification Search
CPC .......... G06T 7/337; G06T 2207/10028; G06T 2207/20081; G06T 2207/20084; G06T 2207/10072; G06T 2207/30056; G06T 2207/30084; G06T 7/33; G16H 30/20; G16H 30/40; G16H 50/20
See application file for complete search history.

(56) References Cited

U.S. PATENT DOCUMENTS

| | | | |
|---|---|---|---|
| 2022/0414821 A1* | 12/2022 | Zhu ........................... | G06T 7/37 |
| 2023/0289984 A1* | 9/2023 | Reaungamornrat ...... | G06T 7/11 |
| 2024/0078690 A1* | 3/2024 | Reaungamornrat ... | G16H 30/20 |
| 2024/0152756 A1* | 5/2024 | Lakshmanan .......... | G06N 3/084 |

OTHER PUBLICATIONS

Learning dense correspondences for non-rigid point clouds with two stage regression. Kangkan Wang. 2021.*
Coherent point drift networks: unsupervised learning of non-rigid point set registration. Lingjing Wang. 2019.*
(Continued)

*Primary Examiner* — Md K Talukder

(57) ABSTRACT

Systems and methods for registering a plurality of medical images are provided. A plurality of partial point clouds of anatomical objects is received. Each of the plurality of partial point clouds is extracted from a respective one of a plurality of medical images. A set of missing points is generated for each of the plurality of partial point clouds. A measure of certainty is generated for each point in 1) the plurality of partial point clouds and 2) the sets of missing points. One or more transformations aligning the plurality of partial point clouds is determined based on the measures of certainty using a machine learning based point registration network for registering the plurality of medical images. The one or more transformations are output.

20 Claims, 14 Drawing Sheets

(56) References Cited

OTHER PUBLICATIONS

Wang et al., "Coherent Point Drift Networks: Unsupervised Learning of Non-Rigid Point Set Registration", arXiv:1906.03039, 2019, 12 pgs.
de Vos et al., "Mutual information for unsupervised deep learning image registration", Proceedings of SPIE Medical Imaging, 2020, 7 pgs.
Groß et al., "AlignNet-3D: Fast Point Cloud Registration of Partially Observed Objects", Proceedings—2019 International Conference on 3D Vision, 2019, 10 pgs.
Haskins et al., "Deep learning in medical image registration: a survey", arXiv:1903.02026, 2020, 30 pgs.
Xue et al., "Lung 4D CT Image Registration Based on High-Order Markov Random Field", IEEE Transactions Medical Imaging, 2020, 11 pgs.
Yang et al., "An efficient two-step multi-organ registration on abdominal CT via deep-learning based segmentation," Biomedical Signal Processing and Control, Bimedical Signal Processing and Control, 2021, pp. 1-12.
Vishnevskiy et al., "Isotropic Total Variation Regularization of Displacements in Parametric Image Registration", IEEE Trans. Med. Imaging, 2017, 10 pgs.
Reaungamornrat et al., "Deformable image registration with local rigidity constraints for cone-beam CT-guided spine surgery", Physics in Medicine and Biology, 2014, pp. 3761-3787.
Staring et al., "A rigidity penalty term for nonrigid registration", Medical Physics, 2007, pp. 4098-4108.
Mansi et al., "iLogDemons: A Demons-Based Registration Algorithm for Tracking Incompressible Elastic Biological Tissues", International Journal of Computer Vision Manuscript, 2011, 18 pgs.
Heinrich et al., "MIND: Modality independent neighbourhood descriptor for multi-modal deformable registration", Medical Image Analysis, 2012, 16 pgs.
Heinrich et al., "Towards Realtime Multimodal Fusion for Image-Guided Interventions Using Self-similarities", Medical Imaging Computer Comput. Comput. Assist. Interv., 2013, 8 pgs.
Reaungamornrat et al., "MIND Demons: Symmetric Diffeomorphic Deformable Registration of MR and CT for Image-Guided Spine Surgery", IEEE Transactions on Medical Imaging, 2016, 31 pgs.
Wang et al., "An Unsupervised Convolution Neural Network for Deformable Registration of Mono/Multi-Modality Medical Images," 43rd Annual International Conference of the IEEE Engineering in Medicine & Biology Society, 2021, pp. 3455-3458.
Begum et al., "On Two Algorithms for Multi-Modality Image Registration Based on Gaussian Curvature and Application to Medical Images", IEEE Access, 2021, p. 10586-10603.
Ding et al., "Unsupervised Multi-modality Registration Network Based on Spatially Encoded Gradient Information", arXiv:2105.07392, 2022, 9 pgs.
Huang et al., "A Coarse-to-Fine Deformable Transformation Framework for Unsupervised Multi-Contrast MR Image Registration with Dual Consistency Constraint", IEEE Transactions on Medical Imaging, 2021, 11 pgs.
Wu et al., "A Disentangled Representations based Unsupervised Deformable Framework for Cross-modality Image Registration", 43rd Annual International Conference of the IEEE Engineering in Medicine & Biology Society (EMBC), 2021, pp. 3531-3534.
Blendowski et al., "Weakly-supervised learning of multi-modal features for regularised iterative descent in 3D image registration", Medical Imaging Analysis, 2021, 14 pgs.
Chen et al., "MR to ultrasound image registration with segmentation-based learning for HDR prostate brachytherapy", Medical Physics, 2021, pp. 1-10.
Lu et al., "An instance segmentation-based framework for a large-sized high-resolution remote sensing image registration", Remote Sensing, 2021, 21 pgs.
Alderliesten et al., "A multi-resolution strategy for a multi-objective deformable image registration framework that accommodates large anatomical differences", Medical Imaging, 2014, 7 pgs.
Drobny et al., "Handling non-corresponding regions in image registration", Informatik aktuell, Springer, 2015, pp. 107-112.
Tward et al., "Diffeomorphic Registration With Intensity Transformation and Missing Data: Application to 3D Digital Pathology of Alzheimer's Disease", Frontiers in Neuroscience, 2018, 15 pgs.
Nithiananthan et al., "Extra-dimensional Demons: A method for incorporating missing tissue in deformable image registration", Medical Physics, 2012, pp. 5718-5731.
Zeineldin et al., "IRegNet: Non-rigid registration of MRI to interventional US for brain-shift compensation using convolutional neural networks", IEEE Access, 2021, pp. 147579-147590.
Zhu et al., "Test-Time Training for Deformable Multi-Scale Image Registration", IEEE International Conference on Robotics and Automation, 2021, arXiv:2103.13578v1, 8 pgs.
Hu et al., "A CNN-Based Approach for Lung 3D-CT Registration", IEEE Access, 2020, pp. 192835-192843.
Wang et al., "Learning Dense Correspondences for Non-Rigid Point Clouds with Two-Stage Regression", IEEE Transactions on Image Processing, 2021, pp. 8468-8482.
Hirose, "A Bayesian Formulation of Coherent Point Drift", IEEE Transactions on Pattern Analysis and Machine Intellectigence, 2021, pp. 2269-2286.
Fu et al., "Biomechanically constrained non-rigid MR-TRUS prostate registration using deep learning based 3D point cloud matching", Medical Image Analysis, 2021, pp. 1-44.
Li et al., "Lepard: Learning partial point cloud matching in rigid and deformable scenes", arXiv:2111.12591, 2021, pp. 1-6.
Zhao et al., "Point Transformer", Computer Vision Foundation, 2020, pp. 16258-16268.
Guo et al., "PCT: Point cloud transformer", Computational VisualMedia, 2020, pp. 187-199.
Yu et al., "PoinTr: Diverse Point Cloud Completion with Geometry-Aware Transformers", 2021, pp. 12498-12507.
Xiang et al., "SnowflakeNet: Point Cloud Completion by Snowflake Point Deconvolution with Skip-Transformer", arXiv:2108:04444, 2021, 11 pgs.
Li et al., "PointCNN: Convolution On X-Transformed Points", Advances in Neural Information Processing Systems, 2018, 11 pgs.
Qi et al., "PointNet: Deep learning on point sets for 3D classification and segmentation", Proceedings of the 30th IEEE Conference on Computer Vision and Pattern Recognition, 2017, 10 pgs.
Qi et al., "PointNet++: Deep hierarchical feature learning on point sets in a metric space", Advances in Neural Information Processing Systems, 2017, 10 pgs.
Chen et al., "A Simple Framework for Contrastive Learning of Visual Representations", xrXiv:2002.05709, 2020, 11 pgs.
He et al., "Momentum Contrast for Unsupervised Visual Representation Learning", IEEE/CVF Conference on Computer Vision and Pattern Recognition, 2020, pp. 9726-9735.
Zbontar et al., "Barlow Twins: Self-Supervised Learning via Redundancy Reduction", Proceedings of the 38th International Conference on Machine Learning, 2021, 13 pgs.
Tsai et al., "A Note on Connecting Barlow Twins with Negative-Sample-Free Contrastive Learning", arXiv:2104.13712, 2021, 5 pgs.
Oyedotun et al., "Training very deep neural networks: Rethinking the role of skip connections", Neurocomputing, 2021, 24 pgs.
Wang et al., "Adaptive Feature Pyramid Networks for Object Detection", IEEE Access, 2021, pp. 107024-107032.
Shen et al., "Neighbors Do Help: Deeply Exploiting Local Structures of Point Clouds", arXiv:1712.06760, 2018, 11 pgs.
Wang et al., "Attentive Normalization for Conditional Image Generation", arXiv:2004.03828, 2020, 10 pgs.
Perez et al., "FiLM: Visual reasoning with a general conditioning layer", 32nd AAAI Conference on Artificial Intelligence, 2018, pp. 3942-3951.
Michalski et al., "An Empirical Study of Batch Normalization and Group Normalization in Conditional Computation," arXiv:1908.00061, 2019, 12 pgs.
Fan et al., "Adversarially Adaptive Normalization for Single Domain Generalization," IEEE/CVF Conference on Computer Vision and Pattern Recognition, arXiv:2106:01899, 2021, 12 pgs.

(56) References Cited

OTHER PUBLICATIONS

Reaungamornrat et al., "Constrained Multiscale Registration of Non-Correspondent Incomplete Multi-Labeled Point Sets", 2021; Siemens; Prior Art Journal 2021 No. 21, 7 pgs.
U.S. Appl. No. 17/654,323, "Automatic MR-US Prostate Image Fusion Through Semi-Supervised Constrained Learning", filed Mar. 10, 2022, 43 pgs.

* cited by examiner

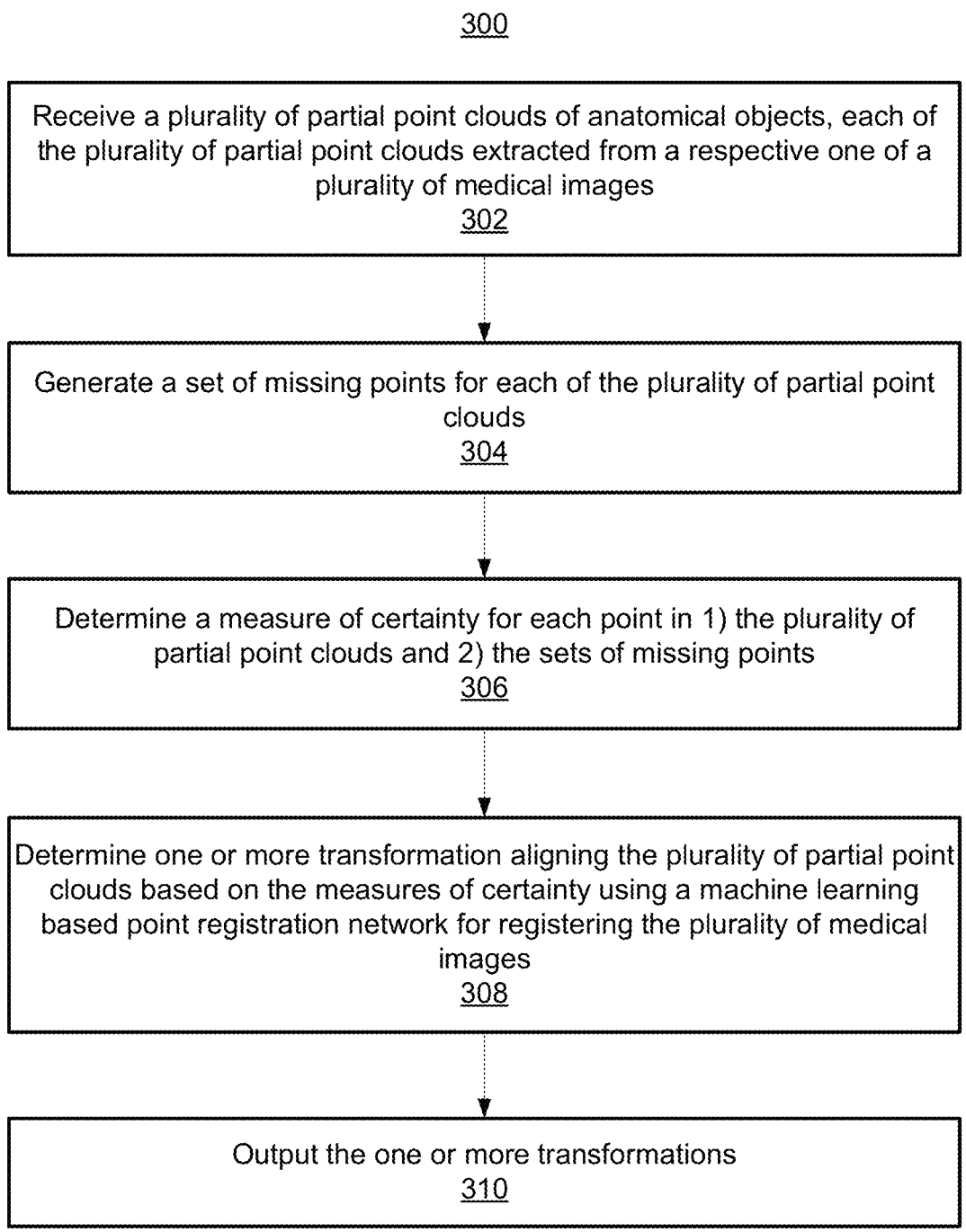

UNSUPERVISED MULTITASK ENSEMBLE FOR SPATIAL TRANSFER OF MULTI-STRUCTURES VIA PARTIAL POINT CLOUD MATCHING

TECHNICAL FIELD

The present invention relates generally to medical image registration, and in particular to an unsupervised multitask ensemble for spatial transfer of multi-structures via partial point cloud matching for medical image registration.

BACKGROUND

Medical image registration is an important step in many medical imaging analysis tasks. Various approaches for medical image registration using artificial intelligence and machine learning have been proposed. However, the performance of medical image registration using artificial intelligence and machine learning remains a challenge due to, for example, mismatch of image content, varying spatial discrepancy of anatomical structures and organs, image quality, contrast differences, complex underlying physical deformation, and computational load.

Conventionally, medical image registration techniques have been proposed with improved computational efficiency and a better ability to resolve large deformation of anatomical structures. However, such conventional medical image registration techniques are unable to handle content inconsistency and discern different tissues. Alternatively, conventional approaches that could address a certain level of content mismatch and/or model certain tissue properties are often computationally expensive and have a limited ability to handle spatially varying motion. Such conventional medical image registration techniques are also susceptible to suboptimal image quality and contrast differences.

BRIEF SUMMARY OF THE INVENTION

In accordance with one or more embodiments, systems and methods for registering a plurality of medical images are provided. A plurality of partial point clouds of anatomical objects is received. Each of the plurality of partial point clouds is extracted from a respective one of a plurality of medical images. A set of missing points is generated for each of the plurality of partial point clouds. A measure of certainty is generated for each point in 1) the plurality of partial point clouds and 2) the sets of missing points. One or more transformations aligning the plurality of partial point clouds is determined based on the measures of certainty using a machine learning based point registration network for registering the plurality of medical images. The one or more transformations are output.

In one embodiment, the set of missing points is generated using a machine learning based point cloud completion network and the measure of certainty is determined using a machine learning based point certainty estimation network. The machine learning based point cloud completion network, the machine learning based point certainty estimation network, and the machine learning based point registration network comprise a shared encoder.

In one embodiment, A) a set of features is extracted from the respective partial point cloud via the shared encoder and B) the sets of missing points are received as input of a point certainty estimation decoder of the machine learning based point certainty estimation network. The measure of certainty for each point in the respective partial point cloud and the sets of missing points is generated as output based on the set of features and the sets of missing points.

In one embodiment, a set of features extracted from the respective partial point cloud via the shared encoder is received as input of a point certainty estimation decoder of the machine learning based point certainty estimation network. The sets of missing points can be received via conditional layers of the point certainty estimation decoder. The measure of certainty is generated as output for each point in the respective partial point cloud and the sets of missing points based on the set of features and the sets of missing points.

In one embodiment, the sets of missing points are generated from the plurality of partial point clouds by transferring local shape features from the shared encoder to a point cloud completion decoder of the machine learning based point cloud completion network via at least one of skip connections or a feature pyramid.

In one embodiment, the one or more transformations are determined by aggregating global and local shape features from the shared encoder with the measures of certainty and determining the one or more transformations based on the aggregated global and local shape features and measures of certainty.

In one embodiment, the shared encoder is trained with at least one of self-supervised and contrastive learning methods in a generative adversarial network framework with adversarial learning.

In one embodiment, the machine learning based point cloud completion network is trained with adversarial learning using a multiscale discriminator. The discriminator discriminates between a completed point cloud generated by the machine learning point cloud completion network and a ground truth complete point cloud.

In one embodiment, the machine learning based point registration network is trained with soft constraints and/or hard constraints based on prior knowledge on transformations and tissue properties, including but not limited to rigid motion of bone, incompressibility (such as, e.g., of muscle and myocardium), topology preservation, and sliding motion of the anatomical structures.

These and other advantages of the invention will be apparent to those of ordinary skill in the art by reference to the following detailed description and the accompanying drawings.

BRIEF DESCRIPTION OF THE DRAWINGS

FIG. 3 shows a method for registering a plurality of medical images using an ensemble of machine learning based networks, in accordance with one or more embodiments;

DETAILED DESCRIPTION

Figure 1:
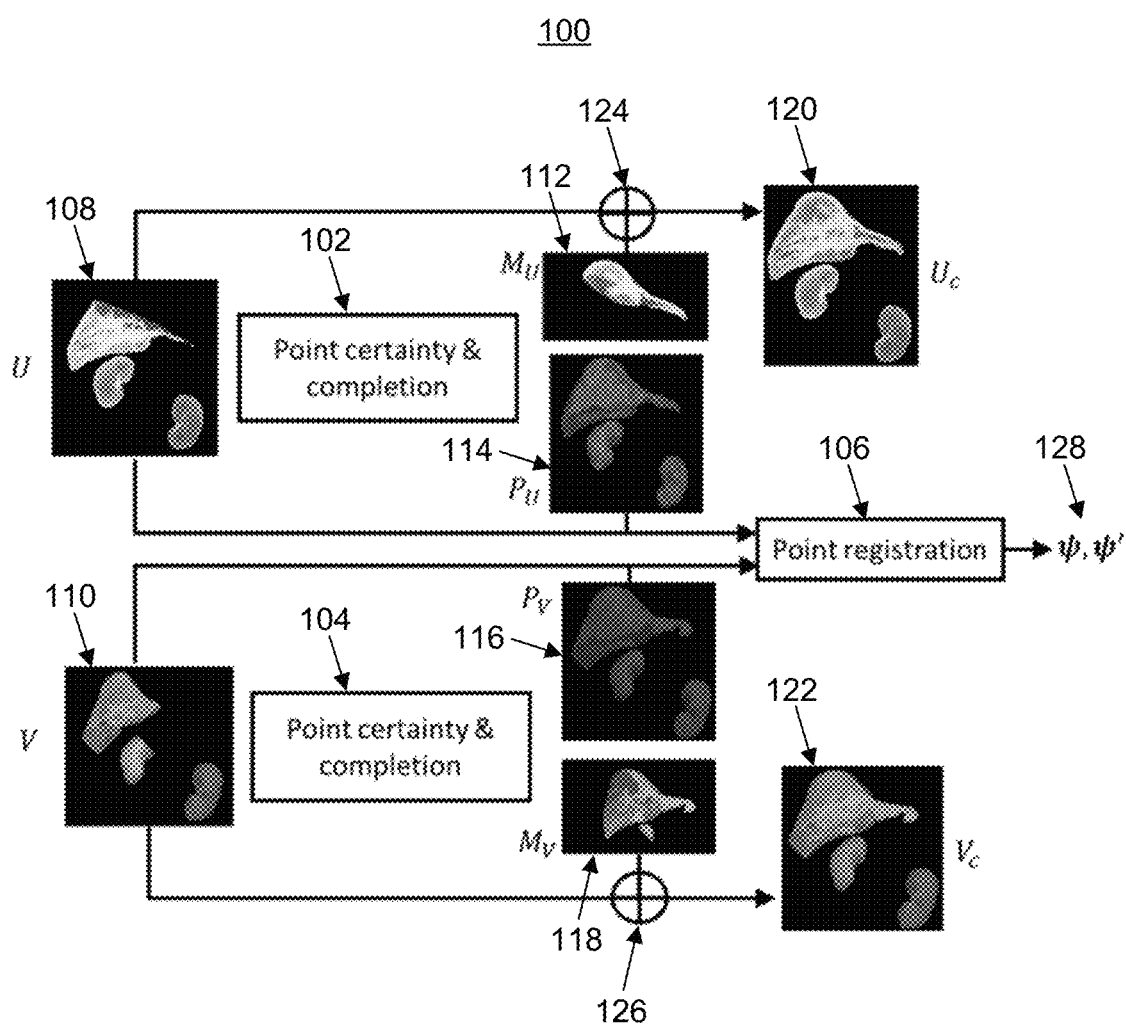
FIG. 1 shows a framework for registering a plurality of medical images using an ensemble of machine learning based networks, in accordance with one or more embodiments.

The present invention generally relates to methods and systems for an unsupervised multitask ensemble for spatial transfer of multi-structures via partial point cloud matching for medical image registration. Embodiments of the present invention are described with respect to the drawings where like reference numerals represent the same or similar elements. Embodiments of the present invention are described herein to give a visual understanding of such methods and systems. A digital image is often composed of digital representations of one or more objects (or structures or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a multi-task, multi-structure ensemble of machine learning based networks for estimating spatial mappings between multiple anatomical objects of interest in a plurality of medical images for registering the plurality of medical images. Unlike conventional intensity-based registration approaches, the ensemble operates on partial point clouds (or point sets) of the anatomical objects of interest, which are derived from segmentations of the anatomical objects of interest from the medical images. As the point clouds are used to drive registration in a deep-learning framework, the ensemble can resolve large deformation while minimizing computation time and are therefore applicable to real time applications. The ensemble is invariant to image contrast and poor image quality since it operates on point clouds, not image intensity.

FIG. 1 shows a framework 100 for registering a plurality of medical images using an ensemble of machine learning based networks, in accordance with one or more embodiments. As shown in framework 100, the ensemble operates on partial point cloud U 108 and partial point cloud V 110 of multiple anatomical objects of interest. Partial point clouds U 108 and V 110 are derived from segmentations of the anatomical objects of interest from the plurality of medical images to be registered. The ensemble comprises 1) a point cloud completion network for completing missing points in the partial point clouds U 108 and V 110, 2) a point certainty estimation network for assigning a validity probability for each point in the completed point clouds (i.e., partial point clouds combined with the estimated missing points), and 3) a point registration network 106 for estimating linear and nonlinear spatial mappings between the partial point clouds. The point cloud completion network and the point certainty estimation network are represented in FIG. 1 as a combined point certainty and completion networks 102 and 104. While point certainty and completion networks 102 and 104 are separately shown in framework 100 to illustrate the processing of point cloud U 108 and point cloud V 110, it should be understood that point certainty and completion networks 102 and 104 represent the same networks.

As shown in framework 100, point certainty and completion network 102 receives partial point cloud U 108 as input and generates a set of missing points $M_U$ 112 and estimated point certainty $P_U$ 114 as output. Partial point cloud U 108 is combined with set of missing points $M_U$ 112 by combiner 124 (e.g., union, adder) to generate a completed point cloud $U_C$ 120. Estimated point certainty $P_U$ 114 estimates a point certainty probability for each point in partial point cloud U 108 and set of missing points $M_U$ 112 (i.e., each point in completed point cloud $U_C$ 120). Point certainty and completion network 104 receives partial point cloud V 110 as input and generates a set of missing points $M_V$ 118 and estimated point certainty $P_V$ 116 as output. Partial point cloud V 110 is combined with set of missing points $M_V$ 118 by combiner 126 (e.g., union, adder) to generate a completed point cloud $V_C$ 122. Estimated point certainty $P_V$ 116 estimates a point certainty probability for each point in partial point cloud V 110 and set of missing points $M_V$ 118. Point registration network 106 determines transformations $\psi$, $\psi'$ 128 based on partial point clouds U 108 and V 110 and optionally estimated point certainty $P_U$ 114 and $P_V$ 116. Transformations $\psi$, $\psi'$ 128 respectively represents the forward and backward transformations for transforming partial point cloud U 108 to align with partial point cloud V 110 and for transforming partial point cloud V 110 to align with partial point cloud U 108 for registering the medical images.

Point certainty and completion network 102 and 104 (i.e., the point certainty estimation network and the point cloud completion network) are trained using self-supervised and/or contrastive learning. The self-supervised and contrastive training of point certainty and completion network 102 and 104 instills invariance to content mismatch. To further enhance the content mismatch invariance of the ensemble (and therefore the registration), point certainty and completion network 102 and 104 can be trained in a generative adversarial network framework. Point registration network 106 is trained using unsupervised learning under geometric-alignment and physics-based constraints, such as, e.g., landmark matching and constraints designed to model the underlying physical deformation (e.g., topology preservation, deformation discontinuity from organ sliding, rigid motion of bone, and incompressibility of certain tissue (e.g., muscle and myocardium)). The unsupervised training of the point registration network 106 mitigates the requirement of large, annotated training data. The ensemble of point certainty and completion network 102 and 104 and point registration network 106 can be trained in an end-to-end manner, as well as separately in an unsurprised manner.

Figure 2:
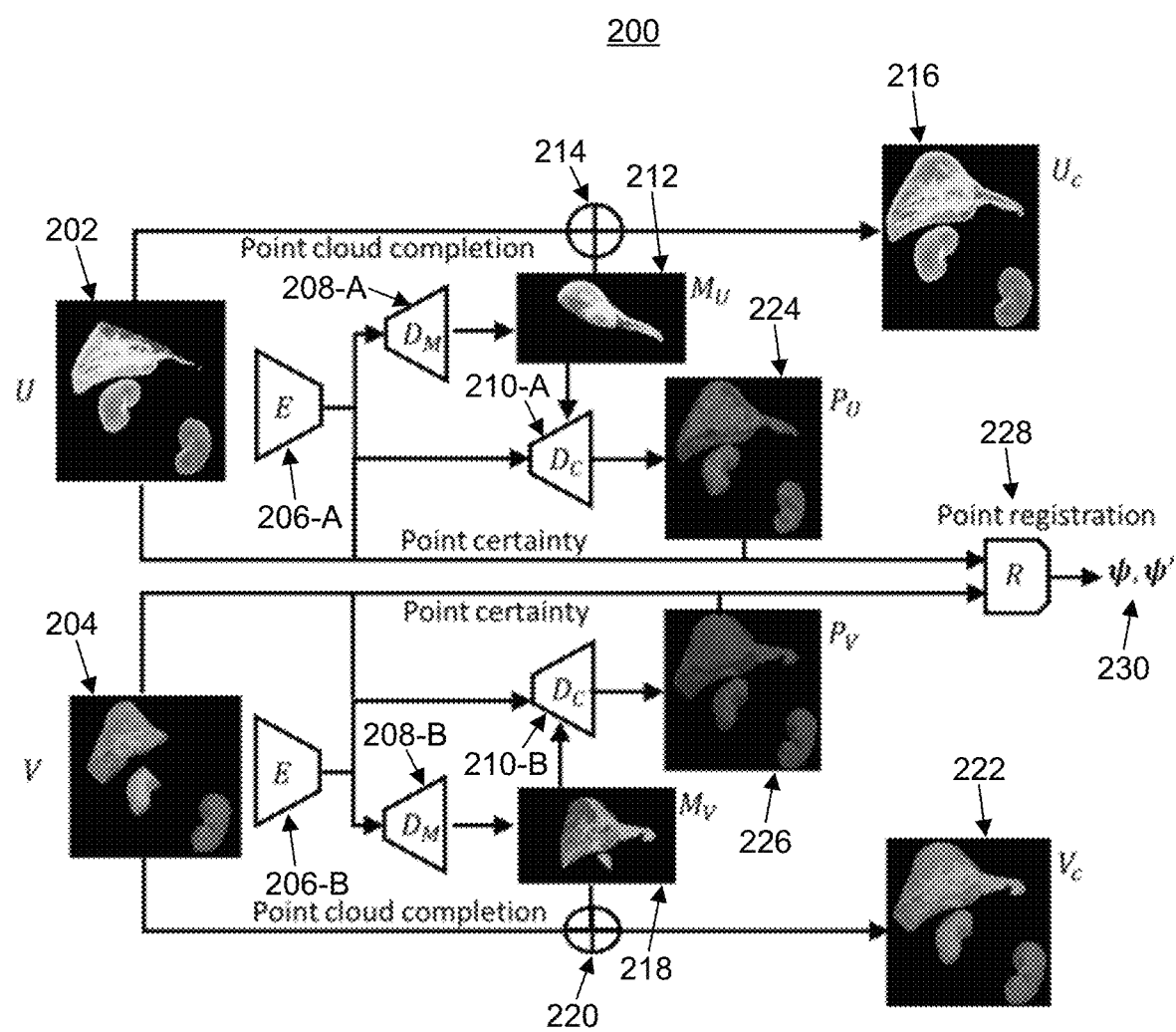
FIG. 2 shows a network architecture of an ensemble of machine learning based networks for registering a pair of input medical images, in accordance with one or more embodiments.

FIG. 2 shows a network architecture 200 of an ensemble of machine learning based networks for registering a pair of input medical images, in accordance with one or more embodiments. Network architecture 200 of FIG. 2 shows the architecture for implementing the machine learning based point cloud completion network, the point certainty estimation network, and point registration network. Network architecture 200 comprises shared encoders E 206-A and 206-B (collectively referred to as shared encoder E 206) (shared between the point cloud completion network, the point certainty estimation network, and point registration network), point cloud completion decoders $D_M$ 208-A and 208-B (collectively referred to as point cloud completion decoder $D_M$ 208), point certainty estimation decoders $D_C$ 210-A and 210-B (collectively referred to as point certainty estimation decoder $D_C$ 210), and registration network R 228. While encoders E 206-A and 206-B, point cloud completion decoders $D_M$ 208-A and 208-B, and point certainty estimation decoders $D_C$ 210-A and 210-B are separately shown to illustrate the processing of partial point clouds U 202 and V 204, it should be understood that encoders E 206, point cloud completion decoders $D_M$ 208, and point certainty estimation decoders $D_C$ 210 each respectively represent the same network.

In one embodiment, encoder E 206 comprises one or more structure-specific encoders $E^S$ for each anatomical object of interest S, which may benefit imposition of a multi-structure constraint. Encoder E 206, point cloud completion decoder $D_M$ 208, point certainty estimation decoder $D_C$ 210, and transformation regression network R 228 may be implemented as a variant of point transformers, Point CNN, PointNet, PointNet++, a combination of: 1D convolutional layers, MLPs (multi-layer perceptrons), multiple modules of transformers, and/or any other suitable machine learning based networks. To make the ensemble invariant to permutation of points in the point clouds, encoder E 206 can incorporate attention modules, transformer-attention modules, transformers, pooling (e.g., max-pooling), etc. Network architecture 200 of FIG. 2 is further described below in connection with FIG. 3.

FIG. 3 shows a method 300 for registering a plurality of medical images using an ensemble of machine learning based networks, in accordance with one or more embodiments. The steps of method 300 may be performed by one or more suitable computing devices, such as, e.g., computer 1302 of FIG. 13. Method 300 of FIG. 3 will be described with continued reference to network architecture 200 of FIG. 2.

At step 302 of FIG. 3, a plurality of partial point clouds of anatomical objects of interest is received. Each of the partial point clouds are extracted from a respective one of a plurality of medical images. The plurality of medical images is the medical images to be registered according to method 300 of FIG. 3. In one example, as shown in FIG. 2, the plurality of partial point clouds is partial point clouds U 202 and V 204 in network architecture 200. The anatomical objects of interest may be any organ, bone, lesion, or any other suitable anatomical objects.

Each partial point cloud is an incomplete set of points representing anatomical objects of interest depicted in the plurality of medical images. Each point is associated with a position (e.g., Cartesian coordinates), e.g., in 2D (two-dimensional) or 3D (three-dimensional) space. The partial point clouds may be generated using any suitable approach. In one embodiment, the partial point clouds are generated based on a segmentation of the anatomical objects of interest from the plurality of medical images. The plurality of partial point clouds may be received by loading previously acquired medical images from a storage or memory of a computer system or receiving medical images that have been transmitted from a remote computer system.

The plurality of medical images may be of the same or different modalities and may be acquired at a same time or at different times. The plurality of medical images may be of any suitable modalities, such as, e.g., CT (computed tomography), CBCT (cone-beam CT), MRI (magnetic resonance imaging), ultrasound, x-ray, and/or any other medical imaging modalities or combinations of medical imaging modalities. The plurality of medical images may be 2D images or 3D volumes.

At step 304 of FIG. 3, a set of missing points is generated for each of the plurality of partial point clouds. In one embodiment, the set of missing points is generated using a machine learning based point cloud completion network. The point cloud completion network may be implemented using any suitable machine learning based architecture.

In one example, as shown in FIG. 2, the point cloud completion network comprises shared encoder 206 and point cloud completion decoder $D_M$ 208 of network architecture 200. Shared encoder 206 separately receives partial point clouds U 202 and V 204 as input and respectively generates sets of features as output. The features are latent features that are invariant to permutation of points and mismatch of content. Point cloud completion decoder $D_M$ 208 separately receives the sets of features as input and respectively generates sets of missing points $M_U$ 212 and $M_V$ 218.

In one embodiment, partial point clouds U 202 and V 204 are respectively combined with sets of missing points $M_U$ 212 and $M_V$ 218 via combiner (e.g., union, adder) 220 to generate completed point clouds $U_C$ 216 and $V_C$ 222. Formally, this is expressed as $U_C = M_U \cup U$ and $U_C = M_V \cup V$, where $\cup$ is a set union operator.

At step 306 of FIG. 3, a measure of certainty (or uncertainty) is determined for each point in 1) the plurality of partial point clouds and 2) the sets of missing points. In one embodiment, the measures of certainty are determined using a machine learning based point certainty estimation network. The point certainty estimation network may be implemented using any suitable machine learning based architecture.

In one example, as shown in FIG. 2, the point certainty estimation network comprises shared encoder E 206 and point certainty estimation decoder $D_C$ 210 of network architecture 200. Point certainty estimation decoder $D_C$ 210 separately receives the sets of features (from shared encoder 206) as input and respectively generates measures of certainty (or uncertainty) $P_U$ 224 and $P_V$ 226 based on sets of missing points $M_U$ 212 and $M_V$ 218. Sets of missing points $M_U$ 212 and $M_V$ 218 may be passed to point certainty estimation decoder $D_C$ 210 either as input to point certainty estimation decoder $D_C$ 210 with the sets of features or as a condition via conditional layers (e.g., attentive normalization, feature-wise linear modulation, conditional batch/group normalization, etc.) in point certainty estimation decoder $D_C$ 210. Point certainty estimation decoder $D_C$ 210 use partial point clouds U 202 and V 204 and sets of missing points $M_U$ 212 and $M_V$ 218 to respectively approximate measures of certainty $P_U$ 224 and $P_V$ 226 for each point in partial point clouds U 202 and V 204 and sets of missing points $M_U$ 212 and $M_V$ 218 (i.e., for each point in completed point clouds $U_C$ 216 and $V_C$ 222). Measures of certainty $P_U$ 224 and $P_V$ 226 may be probabilities representing a certainty or reliability of respective points. Measures of certainty $P_U$ 224 and $P_V$ 226 may be represented as a probability map or in any other suitable forms.

Figure 5:
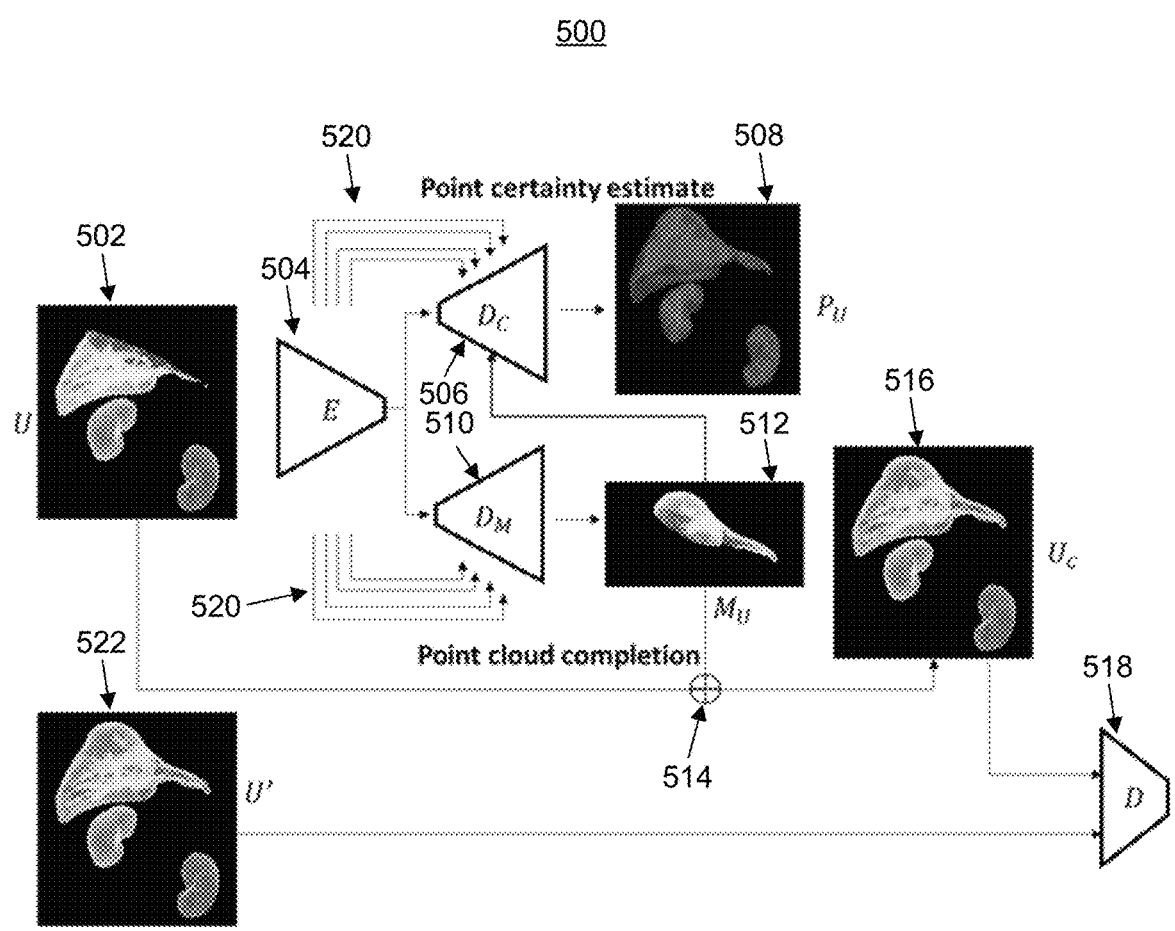
FIG. 5 shows a framework for training a point cloud completion network in a GAN with adversarial learning, in accordance with one or more embodiments.

Bottleneck features, which are output from the last block/layer of shared encoder E 206, may capture only global shape information since detailed/local shape features may be lost as the features pass through multiple blocks/layers of shared encoder E 206. In one embodiment, as shown in FIG. 5 (described in more detail below), skip connections or feature pyramid may be used to transfer multiscale local shape features from shared encoder E 206 to point cloud completion decoder $D_M$ 208 and point certainty estimation decoder $D_C$ 210, improving the network ability to preserved detailed local shape information.

At step 308 of FIG. 3, one or more transformations aligning the plurality of partial point clouds is determined based on the measures of certainty using a machine learning based point registration network for registering the plurality of medical images. The point registration network may be implemented using any suitable machine learning based architecture.

In one example, as shown in FIG. 2, the point registration network comprises shared encoder 206 and transformation regression network R 228. Transformation regression network R 228 receives the sets of features (from shared encoder 206) and measures of certainty $P_U$ 224 and $P_V$ 226 as input and generates linear/nonlinear transformations $\psi, \psi'$ 230 representing forward and backward transformations for transforming partial point clouds U 202 and V 204 to respectively align with partial point clouds V 204 and U 202. Forward transformation $\psi$ transforms partial point cloud U 202 to align with partial point cloud V 204 while backward transformation $\psi'$ transforms partial point cloud V 204 to align with partial point cloud U 202.

In one embodiment, K-nearest neighbor, K-mean, or any other cluster algorithms can be used to group or divide partial point clouds U 202 and V 204 into subregions in which detailed local features can be learned using shared encoder E 206, separate copies of encoders E for each subregion, or a different encoder. The set of local features from each subregion can be combined with multiscale intermediate features (output from different blocks/layers of shared encoder E 206) and global features (output from the last block/layer of shared encoder E 206) to facilitate local and global shape understanding of point cloud completion decoder $D_M$ 208, point certainty estimation decoder $D_C$ 210, and transformation regression network R 228, and thus improve the overall performance of the ensemble.

In one embodiment, transformation regression network R 228 generates transformations $\psi, \psi'$ 230 based on the sets of features (from shared encoder 206) only without using measures of certainty $P_U$ 224 and $P_V$ 226.

At step 310 of FIG. 3, the one or more transformations are outputted. For example, the one or more transformations can be outputted by displaying the one or more transformations on a display device of a computer system, storing the one or more transformations on a memory or storage of a computer system, or by transmitting the one or more transformations to a remote computer system. In one embodiment, the one or more transformations are outputted to a downstream system for performing a medical imaging analysis task.

The point cloud completion network, point certainty estimation network, and point registration network are trained during a prior offline training stage. Once trained, the trained point cloud completion network, trained point certainty estimation network, and trained point registration network are applied during an online or inference stage, for example, for respectively performing steps 304, 306, and 308 of method 300 of FIG. 3.

The point cloud completion network and point certainty estimation network can be trained with self-supervised and/or contrastive learning methods in a GAN (generative adversarial network) framework with adversarial learning to instill invariance to content mismatches in shared encoder 206 and thus the ensemble. The point cloud completion network and point certainty estimation network are trained using a set of training data, such as, e.g., simulated training data.

Figure 4A:
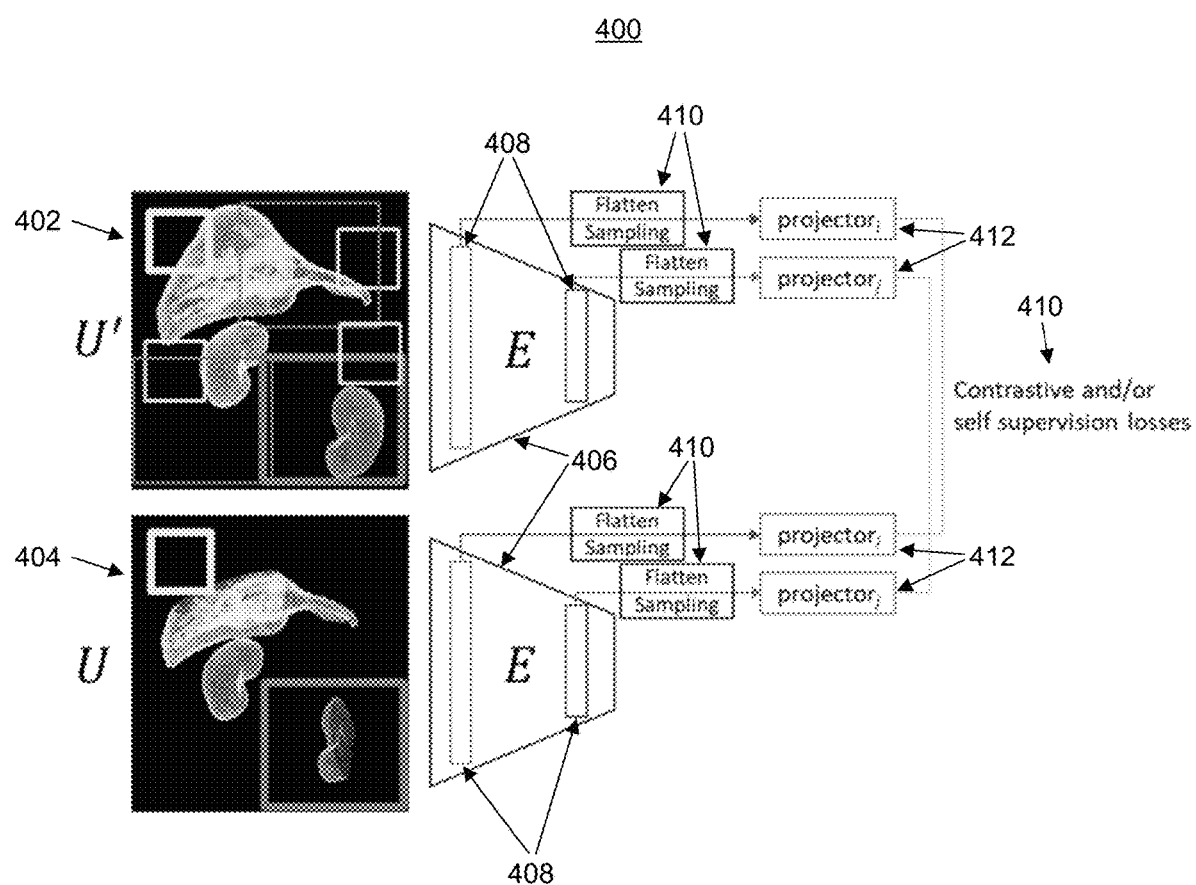
FIG. 4A shows a framework for training a shared encoder E using self-supervised and/or contrastive learning, in accordance with one or more embodiments.

FIG. 4A shows a framework 400 for training a shared encoder E 406 using self-supervised and/or contrastive learning, in accordance with one or more embodiments. In one example, shared encoder E 406 is shared encoder E 206 of FIG. 2. It should be understood that while shared encoders E 406 are separately shown as multiple instances to illustrate the processing of ground truth complete point cloud U' 402 and training partial point cloud U 404, shared encoders E 406 are the same encoder.

Framework 400 illustrates multiscale, multi-FOV (field-of-view) self-supervised and/or contrastive learning of shared encoder E 406 using a set of training data comprising ground truth complete point cloud U' 402 and corresponding training partial point cloud U 404. In one embodiment, the set of training data comprises synthetic or simulated training data. Intermediate features outputted by blocks/layers 408 of shared encoder E 406 are randomly sampled 410 to capture features at different scales and FOVs. Shared projector MLPs 412 are used to project the multi-scale, multi-FOV features (randomly sampled from the intermediate features of shared encoder E 406) into a lower dimensional space in which the similarity between features can be compared using various types of self-supervised and/or contrastive losses 410.

In one embodiment, the loss 410 is a contrastive loss $L_{NCE}$ between a low-dimensional normalized embedding q, its positive normalized counter part $k_+$, and its negative normalized counter parts $k_i$ for i=1, 2, ..., K as defined in Equation 1:

$$L_{NCE} = -\log \frac{\exp(q \cdot k_+/\tau)}{\sum_{i=1}^{K} \exp(q \cdot k_i/\tau)} \quad (1)$$

where $\cdot$ denotes the dot vector product, and $\tau$ is a temperature parameter. The embeddings q, $k_+$, and $k_i$ are normalized so the dot product yields the cosine distance.

In one embodiment, the loss 410 is a self-supervised loss, which is considered negative-sample-free learning. Self-supervised losses can be computed based on, for example, a cross-correlation matrix $C=q^T \cdot k_+$, using, e.g., Barlow Twins' loss $L_B$ as defined in Equation (2):

$$L_B = \sum_i (1 - C_{ii})^2 + \lambda \sum_i \sum_{j \neq i} C_{ij}^2, \quad (2)$$

and Hilbert-Schmidt Independence Criterion $L_H$ as defined in Equation (3):

$$L_H = \sum_i (1 - C_{ii})^2 + \lambda \sum_i \sum_{j \neq i} (1 + C_{ij})^2 \quad (3)$$

where λ is a trade-off parameter controlling the on-diagonal terms (i.e., $C_{ii}$) and off-diagonal terms (i.e., $C_{ij}$ for j≠i).

In one embodiment, the loss 410 is a combined loss $\mathcal{L}_{SSL}$, combining contrastive loss $L_{NCE}$, Barlow Twins' loss $L_B$, and Hilbert-Schmidt Independence Criterion $L_H$, as well as other self-supervised/contrastive losses, for constraining shared encoder E 406 to be invariant to content mismatches, given the set of training data, as defined in Equation (4):

$$\mathcal{L}_{SSL}=\lambda_{NCE}L_{NCE}+\lambda_B L_B+\lambda_H L_H \quad (4)$$

where $\lambda_i$ weighs the strength of each loss $L_i$.

Figure 4B:
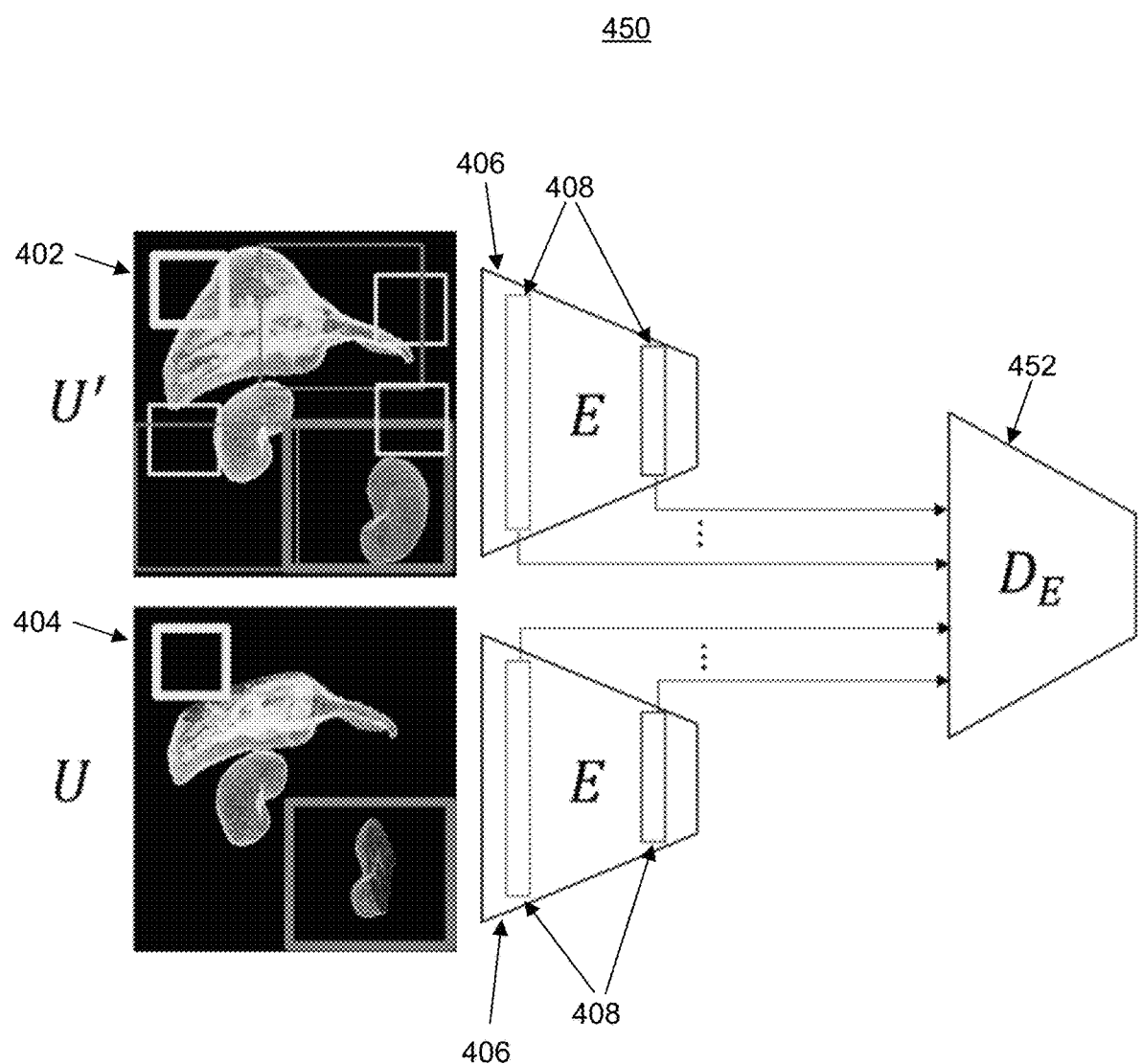
FIG. 4B shows a framework for training a shared encoder E in a GAN with adversarial learning, in accordance with one or more embodiments.

FIG. 4B shows a framework 450 for training a shared encoder E 406 in a GAN with adversarial learning, in accordance with one or more embodiments. As shown in framework 450, a multiscale discriminator $D_E$ 452 is used to encourage shared encoder E 406 to embed a partial point set in the same space as its complete observation. Discriminator $D_E$ 452 receives as input intermediate features outputted by blocks/layers 408 of shared encoder E 406 and attempts to discriminate between features of ground truth complete point cloud U' 402 and corresponding training partial point cloud U 404. The generative adversarial objective functions can be defined as in Equations (5) and (6):

$$L_{D_E}=-\mathbb{E}_{U'}[f(D_E(U,U'))]-\mathbb{E}_{U'}[g(D_E(U,U'))] \quad (5)$$

$$L_E=-\mathbb{E}_{U'}[f(D_E(U,U'))]-\mathbb{E}_{U'}[g(D_E(U,U'))] \quad (5)$$

where $f(\cdot)=\log(\cdot)$ and $g(\cdot)=\log(1-\cdot)$ are, for example, for the optimization of parameters of discriminator $D_E$ 452 and shared encoder E 406, respectively.

FIG. 5 shows a framework 500 for training a point cloud completion network in a GAN with adversarial learning, in accordance with one or more embodiments. In one example, shared encoder E 504, point cloud completion decoder $D_M$ 510, and point certainty estimation decoder $D_C$ 506 of framework 500 are shared encoder E 206, point cloud completion decoder $D_M$ 208, and point certainty estimation decoder $D_C$ 210 respectively.

As shown in framework 500, training partial point cloud U 502 is inputted into shared encoder E 504 to generates a set of features, which are decoded by point cloud completion decoder $D_M$ 510 and point certainty estimation decoder $D_C$ 506 to respectively generate set of missing parts $M_U$ 512 and measures of certainty $P_U$ 508. Skip connections and/or feature pyramid 520 can be used to transfer multiscale local shape features from shared encoder E 504 to point cloud completion decoder $D_M$ 510 and point certainty estimation decoder $D_C$ 506. Set of missing parts $M_U$ 512 is passed to point certainty estimation decoder $D_C$ 506 for estimating measures of certainty $P_U$ 508. Set of missing parts $M_U$ 512 is combined with training partial point cloud U 502 via combiner 514 to generate completed point cloud $U_C$ 516. Multiscale discriminator D 518 attempts to discriminate or distinguish between completed point cloud $U_C$ 516 from the ground truth complete point cloud U' 522. Accordingly, discriminator D 518 forces the generator (i.e., shared encoder E 504 and point cloud completion decoder $D_M$ 510) to generate the distribution of completed point cloud $U_C$ 516 indistinguishable from the distribution of the ground truth complete point cloud U' 522. The GAN losses $L_D$ and $L_G$ for discriminator D 518 and the generator respectively can be defined as in Equations (7) and (8):

$$L_D=-\mathbb{E}_{U'}[f(D(U_c,U'))]-\mathbb{E}_{U_c}[g(D(U_c,U'))] \quad (7)$$

$$L_G=-\mathbb{E}_{U_c}[f(D(U_c,U'))]-\mathbb{E}_{U'}[g(D(U_c,U'))] \quad (8)$$

The point cloud completion network (i.e., shared encoder E 504 and point cloud completion decoder $D_M$ 510) is trained to minimize the distance between the completed point cloud $U_C$ 516 and its corresponding ground truth complete point cloud U'. Ideally, the distance between the completed point cloud $U_C$ 516 and the ground truth complete point cloud U' should be zero. Likewise, the point certainty estimation network (i.e., shared encoder E 504 and point certainty estimation decoder $D_C$ 506) is trained to minimize the difference between measures of certainty $P_U$ 508 and it corresponding ground truth measures of certainty $P_{U'}$. The objective function for training the point cloud completion network and the point certainty estimation network is defined as in Equation (9):

$$\mathcal{L}_{CC}=\lambda_d[d(U_c,U')+d(V_c,V')]+\lambda_m[d(M_U,M'_U)+d(M_V,M'_V)]+\lambda_p[\|P_U-P'_U\|_1+\|P_V-P'_V\|_1]+\mathcal{L}_{SSL}+\lambda_G L_G \quad (9)$$

where $M'_Q$ is a set of ground truth missing point of a partial point cloud Q and $d(\cdot,\cdot)$ is a point-cloud distance (that does not assume known correspondence), such as, e.g., Chamfer distance, Earth Mover's distance, a mixture distribution distance, etc. As setting $\lambda_i$ to 0 disabling a loss i in Equation (9), self-supervision, contrastive, and GAN losses can be turned on and off, offering various training strategies (i.e., self-supervised training, contrastive training, GAN training, or their combinations). To compute mixture distance between point clouds, the mixture distribution may be a Gaussian mixture ϕ comprising n densities located at $\mu_i$ for i=1, 2, . . . , n as in Equation (10):

$$\phi(x\mid\Theta) = \sum_{i=1}^{n} w_i \phi_i(x\mid\mu_i,\Sigma_i) \quad (10)$$

where $\Theta=\{w_i, \mu_i, \Sigma_i\}$ is a set of mixture parameters. The values of the diagonal elements of $\Sigma_i$ can take into account anisotropic image resolution. A multiscale multi-structure $\ell^p$ distance between a mixture $\phi(x|\Theta_{U_c})$ of completed point cloud $U_C$ 516 and $\phi(x|\Theta_{U'})$ of ground truth complete point cloud U' can be computed as in Equation (11):

$$d(U_c, U') = \sum_l \sum_s w_s \mathbb{E}\left[\int [\phi(x\mid\Theta_{U_c}) - \phi(x\mid\Theta_{U'})]^p dx\right] \quad (11)$$

where l denotes a mixture scale, $w_s$ weights the contribution from each structure s, $\Theta_{U_c}\in\{^{U_c}w_i^s, ^{U_c}\mu_i^s, ^{U_c}\Sigma_i^s | s=1, 2, \ldots, S, i=1, 2, \ldots, n\}$ is the mixture parameters for S structures and n points in completed point cloud $U_C$ 516. The sets of mixture parameters of U', V' and $V_c$ can be described similarly. The higher $w_s$, the stronger emphasis on the reconstruction of s (i.e., matching of shape and alignment). The $\ell^p$ Gaussian mixture distance between $V_c$ and V' can be computed in the same manner.

In one embodiment, training data including U, $M_U$, $P_U$, $P'_U$ and V, $M_V$, $P_V$, $P'_V$ can be simulated from known complete pointsets $U'=\{u'_i\}_{i=1}^n$ and $V'=\{v'_i\}_{i=1}^m$, respectively. For instance, to simulate measures of certainty, random linear and/or nonlinear transformations φ can be applied to ground truth complete point cloud U' to form a point set $U=\{u_i=\varphi[u'_i]\}_{i=1}^n$. Since the point certainty probability $p_i$ should be 1 if the distance between $u'_i$ and $u_i=\varphi[u'_i]$ is zero and should decrease as the distance increases, point certainty probability $p_i$ can be approximated using a Gaussian function as defined in Equation (12):

$$p_i=\exp(-\sigma\|u_i-u'_i\|_2^2)=\exp(-\sigma\|\varphi[u'_i]-u'_i\|_2^2), \quad (12)$$

where σ is a scaling factor controlling the width and steepness of the Gaussian function. Other bell-shape-like functions h(·) satisfying h(0)=1 and $$\lim_{|x|\to\infty} h(x) = 0 \text{ (i.e., } h(x)$$

decreases as x moves away from the origin) can be used, such as, e.g., Wendland and Wu radial basis functions. The uncertainty probability is $1-p_i$.

Figure 6:
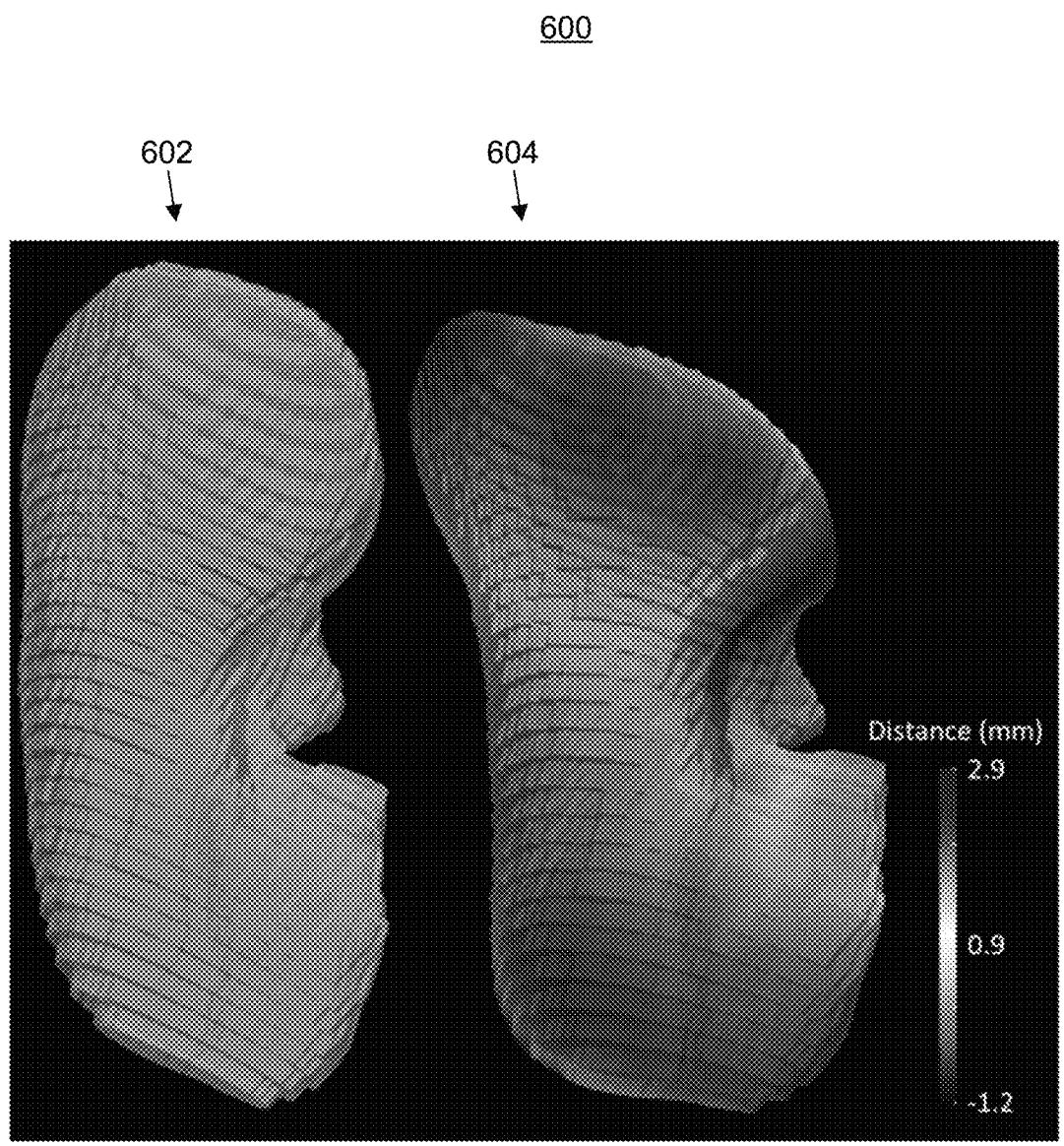
FIG. 6 shows an image illustrating the $\ell^2$ distance between a ground truth $\ell$ complete point cloud $U'=\{u'_i\}_{i=1}^n$ and a transformed complete point cloud $\psi[U']=\{\psi[u'_i]\}_{i=1}^n$, in accordance with one or more embodiments.

FIG. 6 shows an image 600 illustrating the $\ell^2$ distance between a ground truth complete point cloud $U'=\{u'_i\}_{i=1}^n$ 602 and a transformed complete point cloud $\varphi[U']=\{\varphi[u'_i]\}_{i=1}^n$ 604, in accordance with one or more embodiments. In one embodiment, the transformed complete point cloud 604 can be cropped to represent a partial point cloud. In this embodiment, the distance of the missing points can be measured as, e.g., the distances between known missing points and the nearest partial observation.

Figure 7:
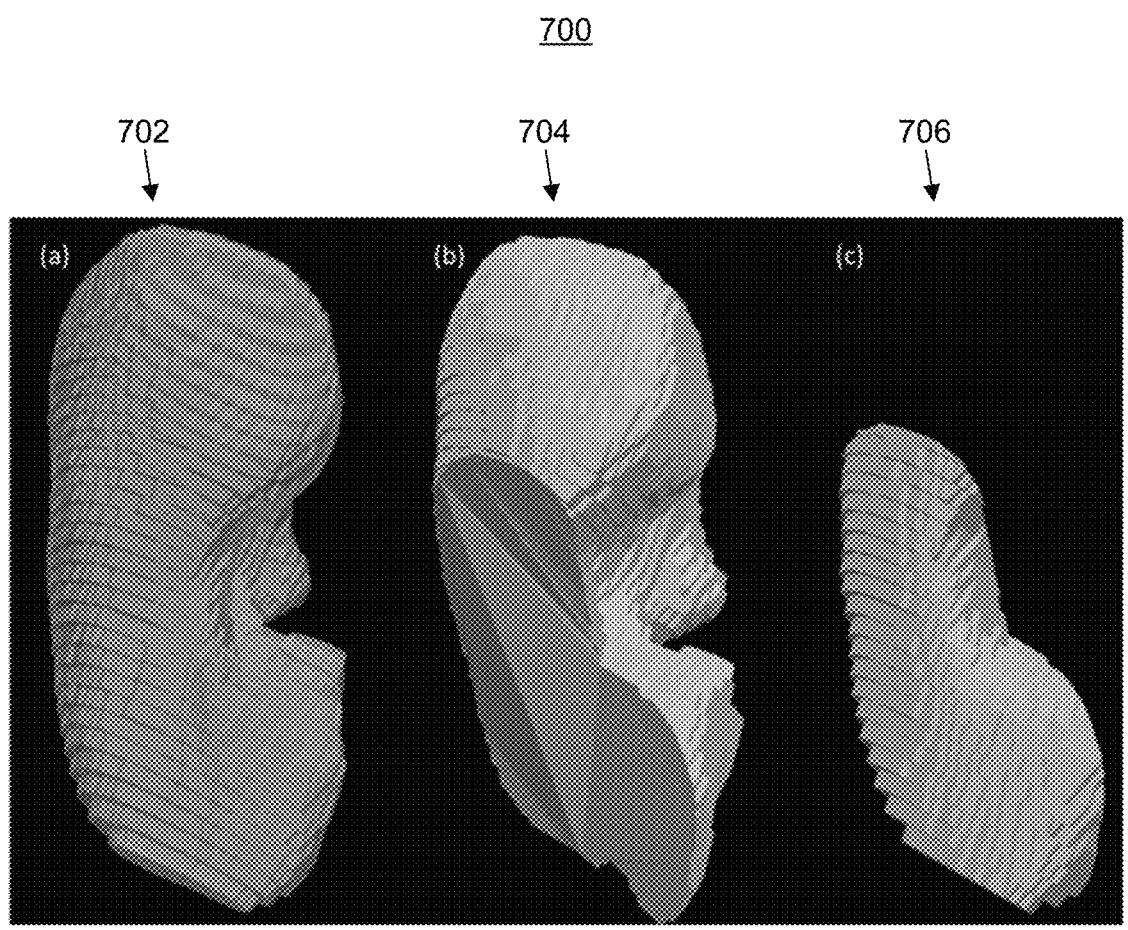
FIG. 7 shows an image 700 illustrating cropping of a ground truth complete point cloud U' and a transformed complete point cloud $\psi[U']$ to generate a partial point cloud, in accordance with one or more embodiments.

FIG. 7 shows an image 700 illustrating (e.g., random) cropping of a ground truth complete point cloud U' to generate a partial point cloud, in accordance with one or more embodiments. Partial point clouds $U=U'\backslash M'_U$ 704 and 706 (where \ denotes the set difference operator) are generated by random cropping of complete point cloud 702 for training the point cloud completion network and the point certainty estimation network. The certainty of missing points in $M'_U$ can be computed as a function of the distance between each known missing point in $M'_U$ and the closest point in the partial point cloud U; because the farther missing points are from the observed point set U, the less certain the missing points are. Alternatively, the combination of both random spatial transforms and random cropping can be used to increase the amount of augmented training data $U=\varphi[U']\backslash\varphi[M'_U]$. In this case, the certainty of missing points in $\varphi[M'_U]$ can be computed as a function of the distance between each point in $\varphi[M'_U]$ and the closest point in $U'\backslash M'_U$. Other approaches for data augmentation, such as, e.g., GAN-based data augmentation, can also be used, with certainty probabilities computed in the similar manner.

The point cloud completion network may be trained separately on its own. The point certainty estimation network, however, is trained with the point-cloud completion network whose parameters can either be fixed or trainable (for fine-tuning), since the point certainty estimation network relies on the missing parts predicted by the point cloud completion network. Both networks can be fine-tuned using (relatively small amount of) annotated data after training on simulated data in self-supervised/contrastive GAN frameworks. In one embodiment, the point cloud completion network and the point certainty estimation network can, additionally, be trained end-to-end with the point registration network.

Figure 8:
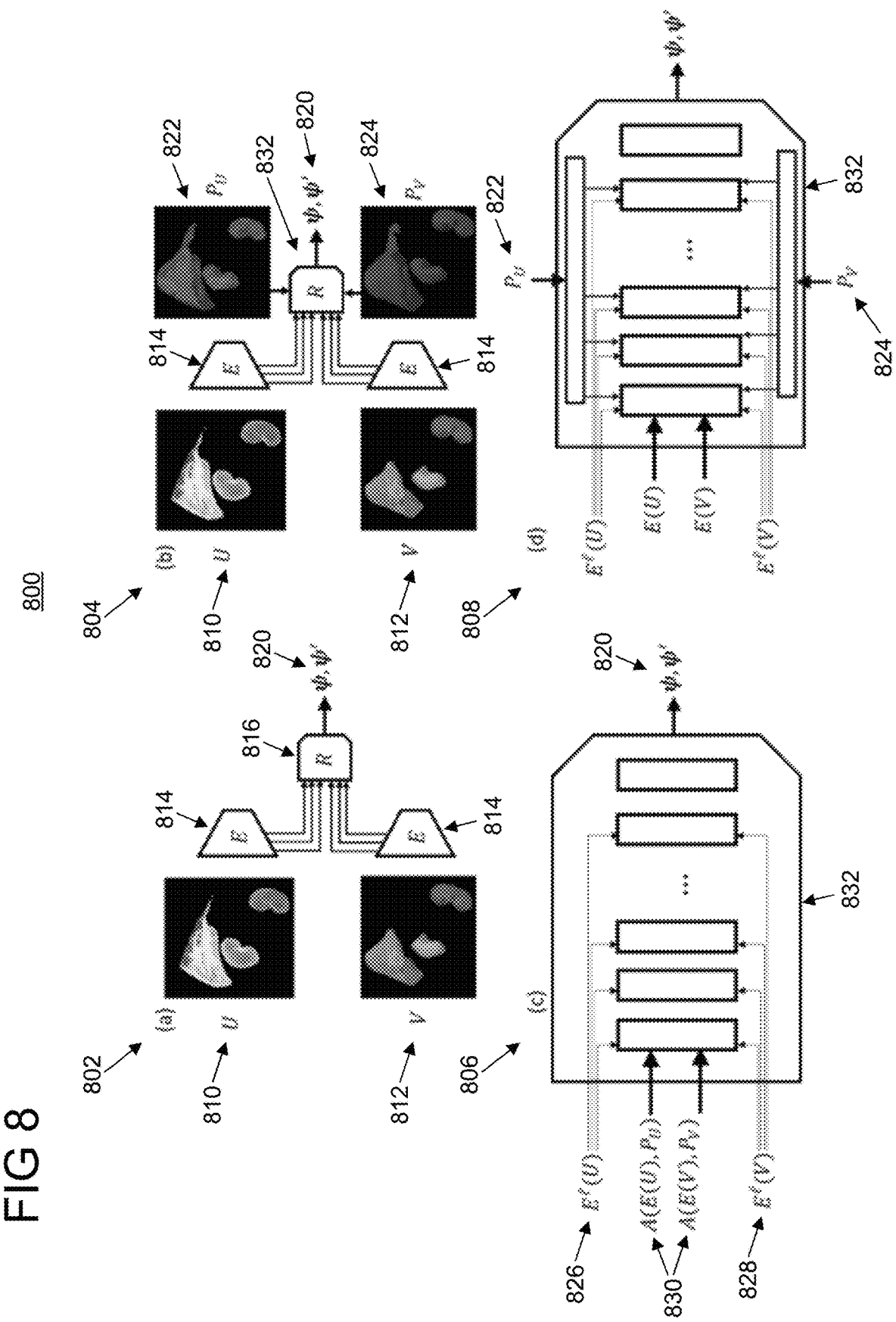
FIG. 8 shows various network architectures of a point registration network, in accordance with one or more embodiments.

FIG. 8 shows various network architectures 800 of a point registration network, in accordance with one or more embodiments. In network architecture 802, transformation regression network R 816 generates linear/nonlinear transformations $\psi,\psi'$ 820 from features extracted from partial point clouds U 810 and V 812 using shared encoder E 814 without measures of certainty $P_U$ and $P_V$. In network architecture 804, transformation regression network R 832 generates linear/nonlinear transformations $\psi,\psi'$ 820 from features extracted from partial point clouds U 810 and V 812 using shared encoder E 814 with measures of certainty $P_U$ 822 and $P_V$ 824. Regression network 816 in the network architecture 802 may share a similar architecture as regression network 832 in network architecture 804 but without $P_U$ 822 and $P_V$ 824 as its input. Regression network 832 in the network architecture 804, on the other hands, may be constructed using architecture similar to the network architectures 806 and 808. In network architecture 806, transformation regression network R 832 generates transformations $\psi,\psi'$ 820 based on bottleneck features E(U) and E(V) detailed/local shape information $E^\ell$ (U) 826 and $E^\ell$ (V) 828 from each block/layer $\ell$ in shared encoder E 814. Global and local features E(U) and $E^\ell$ (U) 826 and E(V) and $E^\ell$ (V) 828 may be respectively aggregated with measures of certainty $P_U$ 822 and $P_V$ 824 using an aggregation function A(·, ·) 830, such as, e.g., concatenation, addition, etc. Additionally, detailed/local shape information $E^\ell$ (U) 826 and $E^\ell$ (V) 828 may be transferred to transformation regression network R 832 using, for example, skip connections or feature pyramid or passed to R 832 as a condition via a conditional layer such as, e.g., feature wise modulation, attentive normalization, conditional batch/group normalization, adaptive normalization, etc. In network architecture 808, transformation regression network R 832 generates transformations $\psi, \psi'$ 820 where detailed/local shape information $E^\ell$ (U) 826 and $E^\ell$ (V) 828 may be inputted to R 832 through skip connections or feature pyramid or as a condition. Measures of certainty $P_U$ 822 and $P_V$ 824 are used to provide condition on registration via a conditional layer such as, e.g., feature wise modulation, attentive normalization, conditional batch/group normalization, adaptive normalization, etc. Also, measures of certainty $P_U$ 822 and $P_V$ 824 may be integrated with global and/or local features using the aggregation function $A(E(U),P_U)$, $A(E^\ell (U),P_U)$ (E(V), $P_V$) and $A(E^\ell$ (V), $P_V$) like the network architecture 806. Transformation regression networks R 816 and 832 may be a variant of Point transformers, PointCNN, PointNet, PointNet++, or a combination of MLPs, feed-forwards networks, 1D convolutional blocks, etc. The output layer of transformation regression networks R 816 and 832 has the same dimension as transformations $\psi,\psi'$ 820. Transformation regression networks R 816 and 832 can approximate both forward $\psi$ and backward $\psi'$ transformations, facilitating imposition of invertibility and topology-preservation priors if required.

Similar to the optimization of the point cloud completion network, the optimal transformation $\psi$ should minimize the distance between $\psi[U]$ and V and similarly, $\psi'$ should minimize the distance between U and $\psi'[V]$. To properly represent the underlying physical deformation, priors on transformation can be imposed as added soft/hard constraints in the objective function, as defined in Equation (13):

$$\ell_R = \lambda_F d(\psi[U],V) + \alpha\lambda_B d(U,\psi'[V]) + \lambda_{R_F} \mathcal{P}(\psi) + \alpha\lambda_{R_B} \mathcal{P}(\psi') \quad (13)$$

subject to H($\psi$) and H($\psi'$) if $\alpha>0$ where $\alpha$ turns on and off the estimation of backward transformation, $\lambda_i$ controls the strength of each penalty, d is a point distance measure between a pair of unknown correspondence point sets (e.g., Chamfer distance, Earth Mover's distance, or a mixture distribution distance), $\mathcal{P}$ (·) denotes a sum of soft constraints on $\psi$ and $\psi'$, and H(·) is a sum of hard constraints on $\psi$ and $\psi'$. To find $\psi$ and $\psi'$ that offer optimal structural alignment, the point distance is computed on all combinations of point-cloud pairs, e.g., U and $V_c$, $M_U$ and V, $U_c$ and $V_c$ after transformation. For example, the $\ell^p$ mixture distance between all point-cloud pairs after $\psi$ transformation can be computed as in Equation (14):

$$d(\psi[U], V) = \sum_{\theta_u}\sum_{\theta_v}\sum_{l}\sum_{s} w_s \mathbb{E}\left[\int [\phi(x|\psi(\theta_u^{s,l})) - \phi(x|\theta_v^{s,l})]^p dx\right], \quad (14)$$

where $\theta_u \in \{\Theta_U, \Theta_{U_c}, \Theta_{U'}, \Theta_{M_U}\}$, $\theta_v \in \{\Theta_V, \Theta_{V_c}, \Theta_{V'}, \Theta_{M_V}\}$, and $\psi$ is the estimated forward transformation. The mixture distance between all point-cloud pairs after $\psi'$ can be derived in the same manner. The measure of certainty of each point, as estimated by the point certainty estimation network, can be used to weight up or down each distribution in the mixture in Equation (10) as $w_i = p_i/\Sigma_j p_j$ (the weights must satisfy $\Sigma_i w_i = 1$), beside passing to transformation regression network R 832 as input or as condition (as in network architectures 804, 806, and 808).

A multi-structure constraint can be accomplished by computing alignment quality per structure similar to Equation (14) or by inputting a partial point cloud of each anatomical object of interest to the ensemble: (i) as an aggregated input, (ii) as a separate input to the shared encoder E 814, or (iii) as a separate input to shared structure-specific shared encoders $E^S$. $\mathcal{P}(\cdot)$ on the other hand, can be used to impose certain transformation properties such as rigid motion of bone. Since the spatial Jacobian of a rigid transformation is a rotation, constraints to force bone to move rigidly can include orthogonality constraints $\mathcal{P}_O$, affinity constraints $\mathcal{P}_A$, and properness constraints $\mathcal{P}_P$:

$$\mathcal{P}_O(\psi,u) = \|\nabla_u \psi^T(u)\nabla_u \psi(u) - I\|_F^2 \quad (15)$$

$$\mathcal{P}_A(\psi,u) = \|\nabla_{uu}\psi(u)\|_F^2 \quad (16)$$

$$\mathcal{P}_P(\psi,u) = (\det(\nabla_u \psi(u)) - 1)^2, \quad (17)$$

where u is a point located in bone and defined in the same space as U, $M_U$, $U_c$, and U'. Let $S_B$ be a set of bony structures such as ribs, femurs, and vertebrae. The rigidity constraints can be imposed per structure as in Equation (18):

$$\mathcal{P}_{Bone} = \sum_{s \in S_B} \lambda_O(s)\mathcal{P}_O(\psi, u_s) + \lambda_A(s)\mathcal{P}_A(\psi, u_s) + \lambda_P(s)\mathcal{P}_P(\psi, u_s), \quad (18)$$

where $\lambda_i(s)$ controls the strength of penalty i at a point $u_s$ on structure $s \in S_B$.

Additionally, since $\det(\nabla_u \psi(x)) = 1$ implies no change in volume, the properness constraint $\mathcal{P}_P$ is also known as a volume preservation constraint or a tissue incompressibility constraint. Thus, if u is a point defined at muscle or soft tissue, Equation (17) imposes incompressibility of the muscle/tissue. Consider a set $S_I$ comprising incompressible organs. An incompressibility constraint $\mathcal{P}_{Inc}$ per organ can be imposed as in Equation (19):

$$\mathcal{P}_{Inc} = \sum_{s \in S_I} \lambda_P(s)\mathcal{P}_P(\psi, u_s) \quad (19)$$

The bone rigidity and incompressibility constraints for backward transforms can be computed in the similar manner. In addition to rigidity of bone and incompressibility, a preservation of topology (i.e., invertibility) constraint $\mathcal{P}_I$ of certain tissue can be imposed in terms of the forward and backward transformations as in Equation (20):

$$\mathcal{P}_I(\psi,\psi',u,v) = \|\psi' \circ \psi(u) - u\| + \|\psi \circ \psi'(v) - v\|, \quad (20)$$

where u is a point located in the tissue of interest and defined in the same space as U, $M_U$, $U_c$, and U', and v is similarly a point located in the tissue of interest and defined in the same space as V, $M_V$, $V_c$, and V'. Let $S_T$ be a set of organs whose topology must be preserved. Equation (20) can be imposed per structure as in Equation (21):

$$\mathcal{P}_T = \sum_{s \in S_T} \lambda_T(s)\mathcal{P}_I(\psi, \psi', u_s, v_s) \quad (21)$$

Figure 9:
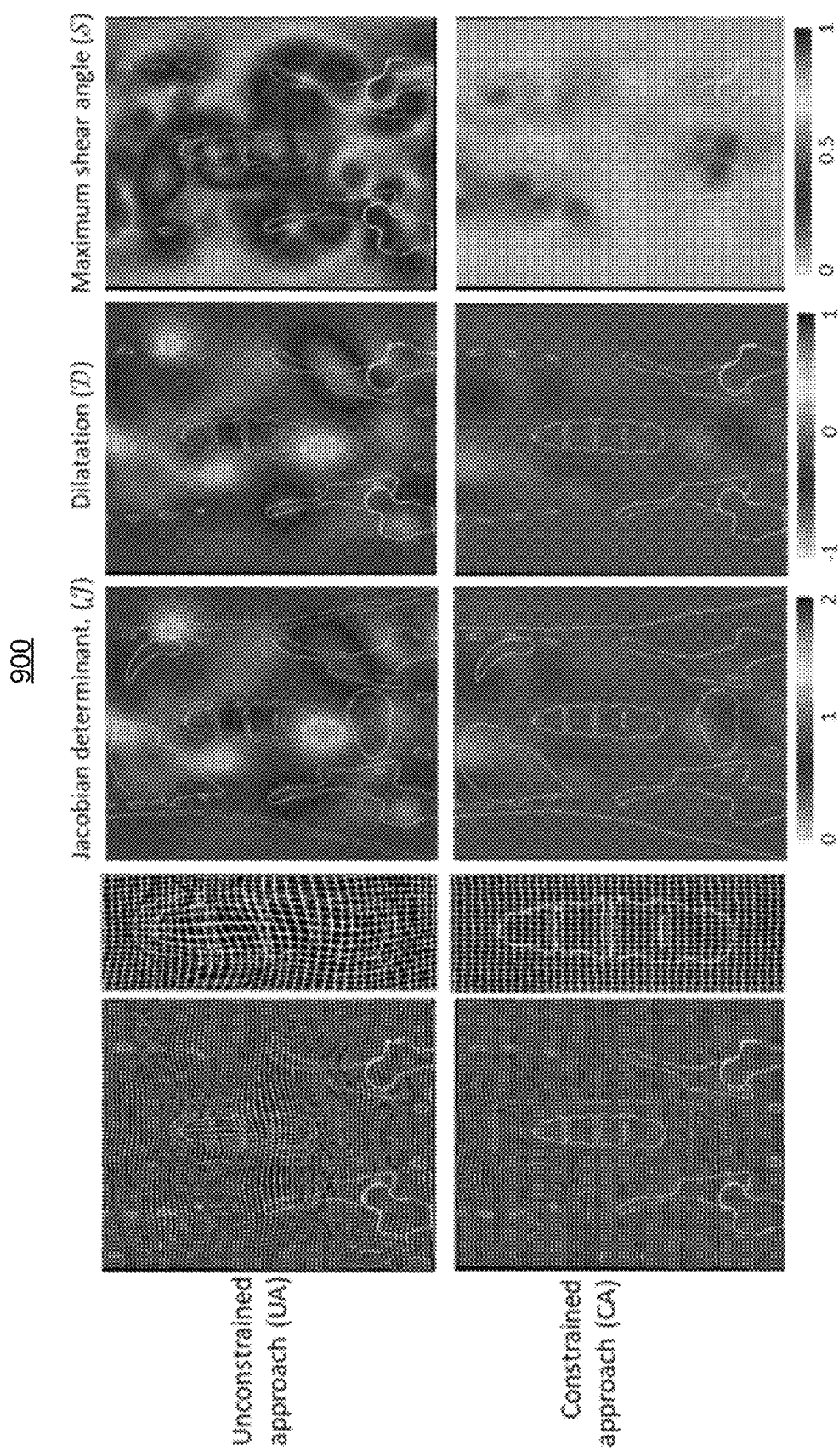
FIG. 9 shows a grid of images illustrating the performance of rigidity constraints of bone and topology-preservation constraints, in accordance with one or more embodiments.

FIG. 9 shows a grid of images 900 illustrating the performance of rigidity constraints and topology-preservation constraints, in accordance with one or more embodiments. The top shows an unconstraint approach as compared to the proposed constrained approach on the bottom. The grid of images 900 after unconstrained and constrained registration illustrate that the proposed rigidity constraints were able to model rigid motion of bone, while resolving deformation of surrounding soft tissue as depicted by the well alignment of the structure contours after registration. The zoomed-in regions of the spine further emphasize the ability of the approach to model bone motions. Additionally, as observable from the map of the determinants of spatial Jacobians $\mathcal{J}$, the constrained approach preserved the volume inside the bone, unlike the unconstrained method. The constrained approach, in addition, estimated topology preservation transformation without introducing implausible tearing or folding of tissue as evident with $\mathcal{J} > 0$ everywhere. Furthermore, dilatation $\mathcal{D}$, measuring local scaling induced by the estimated transformation, confirmed the performance of the proposed approach with $\mathcal{D}$ close to, if not equal to, zero inside the bone. Maximum shear angle $\mathcal{S}$, likewise, demonstrates the ability of the proposed approach to minimize local shear in bone with S close to, if not equal to, zero inside the bone.

Another important spatially-varying local motion is sliding motions of soft tissue organs in the thorax and abdomen, such as, e.g., the lung, liver, and kidneys. Sliding motions are one of the most difficult motions to resolve. The sliding motions may be modelled using the sliding motion constraint $\mathcal{P}_S$ as defined in Equation (22):

$$\mathcal{P}_S(\psi, u, \mathcal{V}) = \left|\frac{(\psi(u) - u) \cdot n}{(r^2 + \epsilon)\|\psi(u) - u\|_2}\right|, \quad (22)$$

for $r = \min(d(u, V))$ where u is a point located at the surface of the organ of interest, V a set of corresponding surface points defined in the same space as V, $M_V$, $V_c$, V', and n is the surface normal vector at u. Equation (22) minimizes the absolute cosine similarity between a surface normal and a displacement at u. The minimization strength is proportional to the inverse square of the distance between u and its closest point in V. Let $S_S$ be a set of soft-tissue organs that can slide against other organs. The sliding-motion constraint can be imposed per structure $s \in S_S$ as in Equation (23):

$$\mathcal{P}_{SM} = \sum_{s \in S_S} \mathcal{P}_S(\psi, u_s, \mathcal{V}_s) \quad (23)$$

The sliding motion constraint on backward transforms $\psi'$ can be defined similarly.

Figure 10:
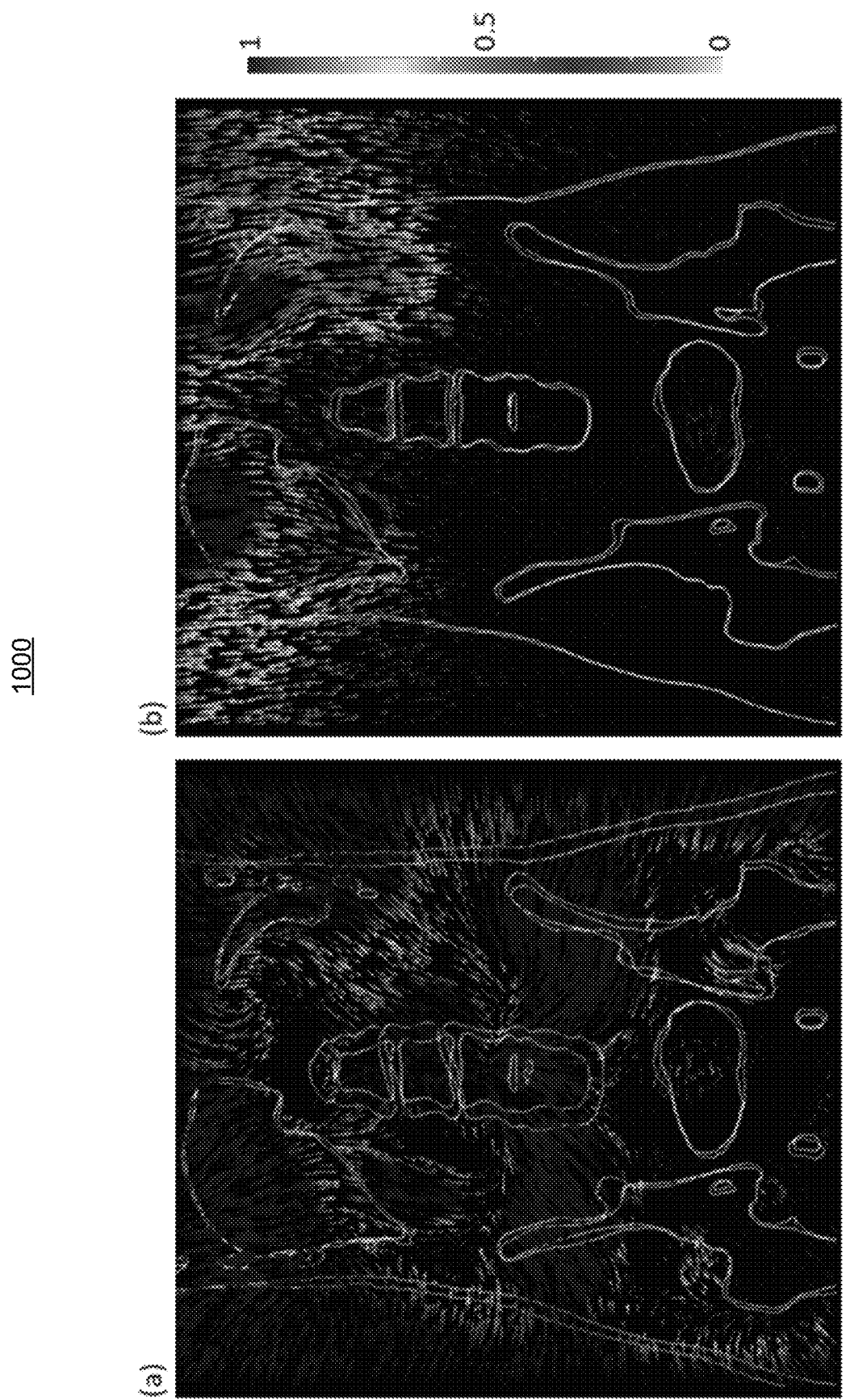
FIG. 10 shows images illustrating the performance of the sliding-motion constraint to resolve breathing motions in dual-energy imaging in which the body of the patient is stationary between the low energy scan and the high energy scan, in accordance with one or more embodiments.

FIG. 10 shows images 1000 illustrating the performance of the sliding-motion constraint to resolve breathing motions in dual-energy imaging in which the body of the patient is stationary between the low energy scan and the high energy scan, in accordance with one or more embodiments. Since the difference in the acquisition time is not large enough to allow motions due to organ fill-up, the lower part of the abdomen stays immobile. In image (a), the unconstrained approach failed to correctly model motions induced purely by respiration. Although the body and the structures in the lower abdomen were stationary, the unconstrained approach mistakenly introduced motions and worsened spatial alignment as observable from the misalignment of the contours of structures after registration. In image (b), the proposed sliding-motion constraint correctly modeled the breathing motions. The constrained approach could, therefore, correctly model immobility of the body and the lower part of the abdomen, unlike the unconstrained approach.

Beside tissue-specific priors, alignment constraints can also be imposed. For example, a landmark constraint can be defined as a soft constraint as in Equation (24):

$$\mathcal{P}_L(\psi) = \sum_{u_L \in U_L, v_L \in V_L} d(u_L, v_L) \tag{23}$$

where $u_L \in U_L$ is a landmark on the point cloud U, $v_L \in V_L$ is a corresponding landmark on the point cloud V, and $d(\cdot,\cdot)$ denotes a distance function between points with known correspondence (e.g., $\ell^p$ distances).

Similarly hard constraints $H(\cdot)$ can be used to impose certain transformation properties. Examples of hard constraints are the unit norm of the quaternion representation q of a rotation $|q|=\sqrt{q^*q}=1$, and the local injectivity of B-splines preventing reflection (causing invalid folding and tearing of tissue), defined as $|v_{ij}|<\sigma_j/K$ for a displacement $v_i$ of a control point i-th where K is a predefined threshold (e.g., K≈2.48 for 3D) and $\sigma_j$ is grid spacing along the j direction.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 11:
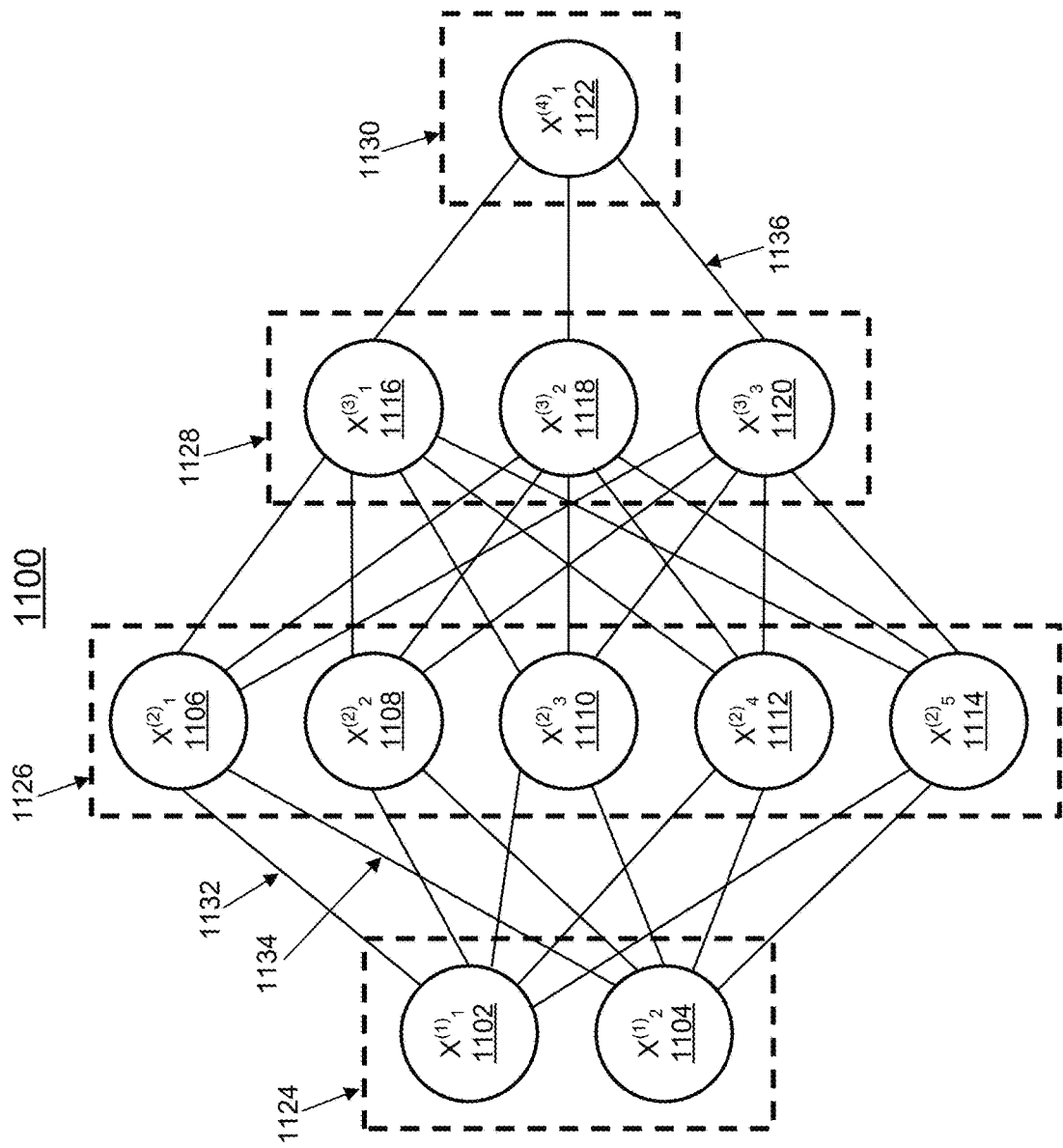
FIG. 11 shows an exemplary artificial neural network that may be used to implement one or more embodiments.

FIG. 11 shows an embodiment of an artificial neural network 1100, in accordance with one or more embodiments. Alternative terms for "artificial neural network" are "neural network", "artificial neural net" or "neural net". Machine learning networks described herein, such as, e.g., point certainty and completion network 102 and 104, and point registration network 106 of FIG. 1; shared encoder E 206, point cloud completion decoder $D_M$ 208, point certainty estimation decoder $D_C$ 210, and registration network R 228 of FIG. 2; the point cloud completion network, point certainty estimation network, and point registration network respectively utilized at steps 304, 306, and 308 of FIG. 3; shared encoder E 406 of FIG. 4A; shared encoder E 406 and discriminator $D_E$ 452 of FIG. 4B; shared encoder E 504, point cloud completion decoder $D_M$ 510, point certainty estimation decoder $D_C$ 510, and discriminator D 518 of FIG. 5; and shared encoder E 814 and regression network R 816 of FIG. 8, may be implemented using artificial neural network 1100.

The artificial neural network 1100 comprises nodes 1102-1122 and edges 1132, 1134, . . . , 1136, wherein each edge 1132, 1134, . . . , 1136 is a directed connection from a first node 1102-1122 to a second node 1102-1122. In general, the first node 1102-1122 and the second node 1102-1122 are different nodes 1102-1122, it is also possible that the first node 1102-1122 and the second node 1102-1122 are identical. For example, in FIG. 11, the edge 1132 is a directed connection from the node 1102 to the node 1106, and the edge 1134 is a directed connection from the node 1104 to the node 1106. An edge 1132, 1134, . . . , 1136 from a first node 1102-1122 to a second node 1102-1122 is also denoted as "ingoing edge" for the second node 1102-1122 and as "outgoing edge" for the first node 1102-1122.

In this embodiment, the nodes 1102-1122 of the artificial neural network 1100 can be arranged in layers 1124-1130, wherein the layers can comprise an intrinsic order introduced by the edges 1132, 1134, . . . , 1136 between the nodes 1102-1122. In particular, edges 1132, 1134, . . . , 1136 can exist only between neighboring layers of nodes. In the embodiment shown in FIG. 11, there is an input layer 1124 comprising only nodes 1102 and 1104 without an incoming edge, an output layer 1130 comprising only node 1122 without outgoing edges, and hidden layers 1126, 1128 in-between the input layer 1124 and the output layer 1130. In general, the number of hidden layers 1126, 1128 can be chosen arbitrarily. The number of nodes 1102 and 1104 within the input layer 1124 usually relates to the number of input values of the neural network 1100, and the number of nodes 1122 within the output layer 1130 usually relates to the number of output values of the neural network 1100.

In particular, a (real) number can be assigned as a value to every node 1102-1122 of the neural network 1100. Here, $x^{(n)}_i$ denotes the value of the i-th node 1102-1122 of the n-th layer 1124-1130. The values of the nodes 1102-1122 of the input layer 1124 are equivalent to the input values of the neural network 1100, the value of the node 1122 of the output layer 1130 is equivalent to the output value of the neural network 1100. Furthermore, each edge 1132, 1134, . . . , 1136 can comprise a weight being a real number, in particular, the weight is a real number within the interval [−1, 1] or within the interval [0, 1]. Here, $w^{(m,n)}_{i,j}$ denotes the weight of the edge between the i-th node 1102-1122 of the m-th layer 1124-1130 and the j-th node 1102-1122 of the n-th layer 1124-1130. Furthermore, the abbreviation $w^{(n)}_{i,j}$ is defined for the weight $w^{(n,n+1)}_{i,j}$.

In particular, to calculate the output values of the neural network 1100, the input values are propagated through the neural network. In particular, the values of the nodes 1102-1122 of the (n+1)-th layer 1124-1130 can be calculated based on the values of the nodes 1102-1122 of the n-th layer 1124-1130 by $$x_j^{(n+1)}{=}f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 1124 are given by the input of the neural network 1100, wherein values of the first hidden layer 1126 can be calculated based on the values of the input layer 1124 of the neural network, wherein values of the second hidden layer 1128 can be calculated based in the values of the first hidden layer 1126, etc.

In order to set the values $w^{(m,n)}_{i,j}$ for the edges, the neural network 1100 has to be trained using training data. In particular, training data comprises training input data and training output data (denoted as ti). For a training step, the neural network 1100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1100 (backpropagation algorithm). In particular, the weights are changed according to $$w'^{(n)}_{i,j}{=}w^{(n)}_{i,j}{-}\gamma \cdot \delta^{(n)}_j \cdot x^{(n)}_i$$

wherein γ is a learning rate, and the numbers $\delta^{(n)}_j$ can be recursively calculated as $$\delta_j^{(n)}{=}(\Sigma_k \delta_k^{(n+1)} \cdot w_{j,k}^{(n+1)}) \cdot f'(\Sigma_i x_i^{(n)} \cdot w_{i,j}^{(n)})$$

$$\delta_j^{(n)}{=}(\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)}{=}(x_k^{(n+1)}{-}t_j^{(n+1)}) \cdot f'(\Sigma_i x_i^{(n)} \cdot w_{i,j}^{(n)})$$

$$\delta_j^{(n)}{=}(x_k^{(n+1)}{-}t_j^{(n+1)}) \cdot f'(\Sigma_i x_i^{(n)} \cdot w_{i,j}^{(n)})$$

if the (n+1)-th layer is the output layer 1130, wherein f' is the first derivative of the activation function, and $y^{(n+1)}_j$ is the comparison training value for the j-th node of the output layer 1130.

Figure 12:
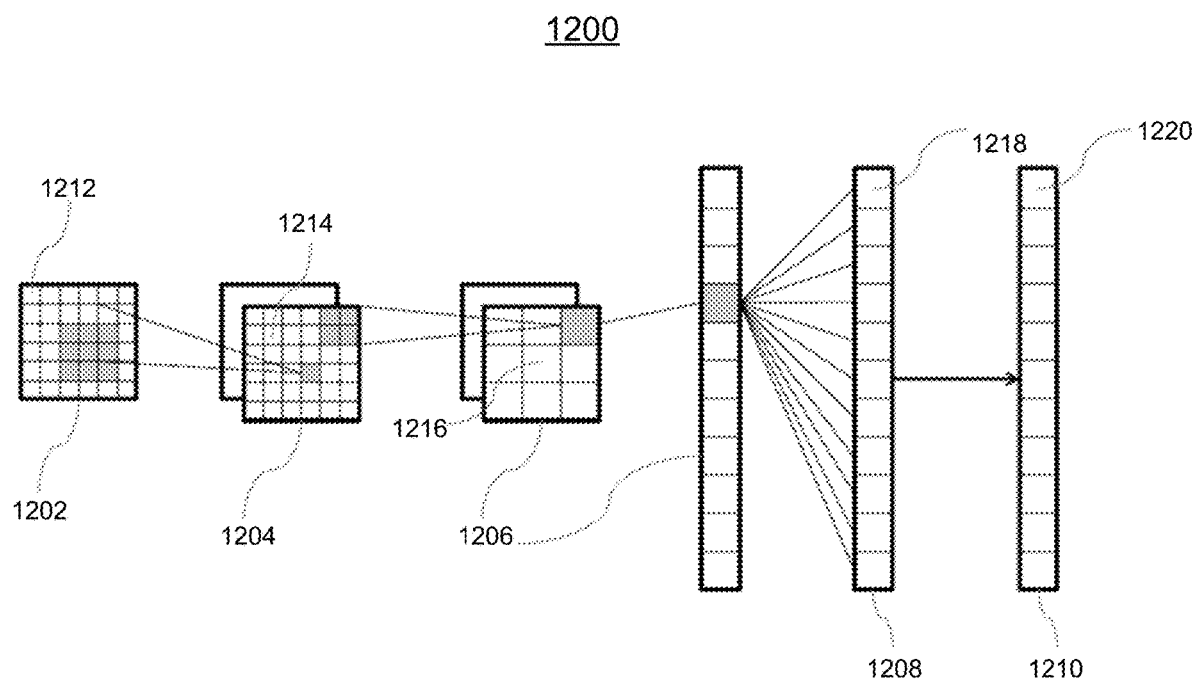
FIG. 12 shows a convolutional neural network that may be used to implement one or more embodiments.

FIG. 12 shows a convolutional neural network 1200, in accordance with one or more embodiments. Machine learning networks described herein, such as, e.g., point certainty and completion network 102 and 104, and point registration network 106 of FIG. 1; shared encoder E 206, point cloud completion decoder $D_M$ 208, point certainty estimation decoder $D_C$ 210, and registration network R 228 of FIG. 2; the point cloud completion network, point certainty estimation network, and point registration network respectively utilized at steps 304, 306, and 308 of FIG. 3; shared encoder E 406 of FIG. 4A; shared encoder E 406 and discriminator $D_E$ 452 of FIG. 4B; shared encoder E 504, point cloud completion decoder $D_M$ 510, point certainty estimation decoder $D_C$ 510, and discriminator D 518 of FIG. 5; and shared encoder E 814 and regression network R 816 of FIG. 8, may be implemented using convolutional neural network 1200.

In the embodiment shown in FIG. 12, the convolutional neural network comprises 1200 an input layer 1202, a convolutional layer 1204, a pooling layer 1206, a fully connected layer 1208, and an output layer 1210. Alternatively, the convolutional neural network 1200 can comprise several convolutional layers 1204, several pooling layers 1206, and several fully connected layers 1208, as well as other types of layers. The order of the layers can be chosen arbitrarily, usually fully connected layers 1208 are used as the last layers before the output layer 1210.

In particular, within a convolutional neural network 1200, the nodes 1212-1220 of one layer 1202-1210 can be considered to be arranged as a d-dimensional matrix or as a d-dimensional image. In particular, in the two-dimensional case the value of the node 1212-1220 indexed with i and j in the n-th layer 1202-1210 can be denoted as $x^{(n)}_{[i,j]}$. However, the arrangement of the nodes 1212-1220 of one layer 1202-1210 does not have an effect on the calculations executed within the convolutional neural network 1200 as such, since these are given solely by the structure and the weights of the edges.

In particular, a convolutional layer 1204 is characterized by the structure and the weights of the incoming edges forming a convolution operation based on a certain number of kernels. In particular, the structure and the weights of the incoming edges are chosen such that the values $x^{(n)}_k$ of the nodes 1214 of the convolutional layer 1204 are calculated as a convolution $x^{(n)}_k{=}K_k{*}x^{(n-1)}$ based on the values $x^{(n-1)}$ of the nodes 1212 of the preceding layer 1202, where the convolution * is defined in the two-dimensional case as $$x_k^{(n)}[i,j]{=}(K_k{*}x^{(n-1)})[i,j]{=}\Sigma_i \Sigma_j K_k[i',j'] \cdot x^{(n-1)}[i{-}i',j{-}j'].$$

Here the k-th kernel $K_k$ is a d-dimensional matrix (in this embodiment a two-dimensional matrix), which is usually small compared to the number of nodes 1212-1218 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1212-1220 in the respective layer 1202-1210. In particular, for a convolutional layer 1204, the number of nodes 1214 in the convolutional layer is equivalent to the number of nodes 1212 in the preceding layer 1202 multiplied with the number of kernels.

If the nodes 1212 of the preceding layer 1202 are arranged as a d-dimensional matrix, using a plurality of kernels can be interpreted as adding a further dimension (denoted as "depth" dimension), so that the nodes 1214 of the convolutional layer 1204 are arranged as a (d+1)-dimensional matrix. If the nodes 1212 of the preceding layer 1202 are already arranged as a (d+1)-dimensional matrix comprising a depth dimension, using a plurality of kernels can be interpreted as expanding along the depth dimension, so that the nodes 1214 of the convolutional layer 1204 are arranged also as a (d+1)-dimensional matrix, wherein the size of the (d+1)-dimensional matrix with respect to the depth dimension is by a factor of the number of kernels larger than in the preceding layer 1202.

The advantage of using convolutional layers 1204 is that spatially local correlation of the input data can exploited by enforcing a local connectivity pattern between nodes of adjacent layers, in particular by each node being connected to only a small region of the nodes of the preceding layer.

In embodiment shown in FIG. 12, the input layer 1202 comprises 36 nodes 1212, arranged as a two-dimensional 6×6 matrix. The convolutional layer 1204 comprises 72 nodes 1214, arranged as two two-dimensional 6×6 matrices, each of the two matrices being the result of a convolution of the values of the input layer with a kernel. Equivalently, the nodes 1214 of the convolutional layer 1204 can be interpreted as arranges as a three-dimensional 6×6×2 matrix, wherein the last dimension is the depth dimension.

A pooling layer 1206 can be characterized by the structure and the weights of the incoming edges and the activation function of its nodes 1216 forming a pooling operation based on a non-linear pooling function f. For example, in the two dimensional case the values $x^{(n)}$ of the nodes 1216 of the pooling layer 1206 can be calculated based on the values $x^{(n-1)}$ of the nodes 1214 of the preceding layer 1204 as $$x^{(n)}[i,j]=f(x^{(n-1)}[id_1,jd_2], \ldots, x^{(n-1)}[id_1+d_1-1,jd_2+d_2-1])$$

In other words, by using a pooling layer 1206, the number of nodes 1214, 1216 can be reduced, by replacing a number d1·d2 of neighboring nodes 1214 in the preceding layer 1204 with a single node 1216 being calculated as a function of the values of said number of neighboring nodes in the pooling layer. In particular, the pooling function f can be the max-function, the average or the L2-Norm. In particular, for a pooling layer 1206 the weights of the incoming edges are fixed and are not modified by training.

The advantage of using a pooling layer 1206 is that the number of nodes 1214, 1216 and the number of parameters is reduced. This leads to the amount of computation in the network being reduced and to a control of overfitting.

In the embodiment shown in FIG. 12, the pooling layer 1206 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1208 can be characterized by the fact that a majority, in particular, all edges between nodes 1216 of the previous layer 1206 and the nodes 1218 of the fully-connected layer 1208 are present, and wherein the weight of each of the edges can be adjusted individually.

In this embodiment, the nodes 1216 of the preceding layer 1206 of the fully-connected layer 1208 are displayed both as two-dimensional matrices, and additionally as non-related nodes (indicated as a line of nodes, wherein the number of nodes was reduced for a better presentability). In this embodiment, the number of nodes 1218 in the fully connected layer 1208 is equal to the number of nodes 1216 in the preceding layer 1206. Alternatively, the number of nodes 1216, 1218 can differ.

Furthermore, in this embodiment, the values of the nodes 1220 of the output layer 1210 are determined by applying the Softmax function onto the values of the nodes 1218 of the preceding layer 1208. By applying the Softmax function, the sum the values of all nodes 1220 of the output layer 1210 is 1, and all values of all nodes 1220 of the output layer are real numbers between 0 and 1.

A convolutional neural network 1200 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1200 can be trained based on the backpropagation algorithm. For preventing overfitting, methods of regularization can be used, e.g. dropout of nodes 1212-1220, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 3. Certain steps or functions of the methods and workflows described herein, including one or more of the steps or functions of FIG. 3, may be performed by a server or by another processor in a network-based cloud-computing system. Certain steps or functions of the methods and workflows described herein, including one or more of the steps of FIG. 3, may be performed by a client computer in a network-based cloud computing system. The steps or functions of the methods and workflows described herein, including one or more of the steps of FIG. 3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
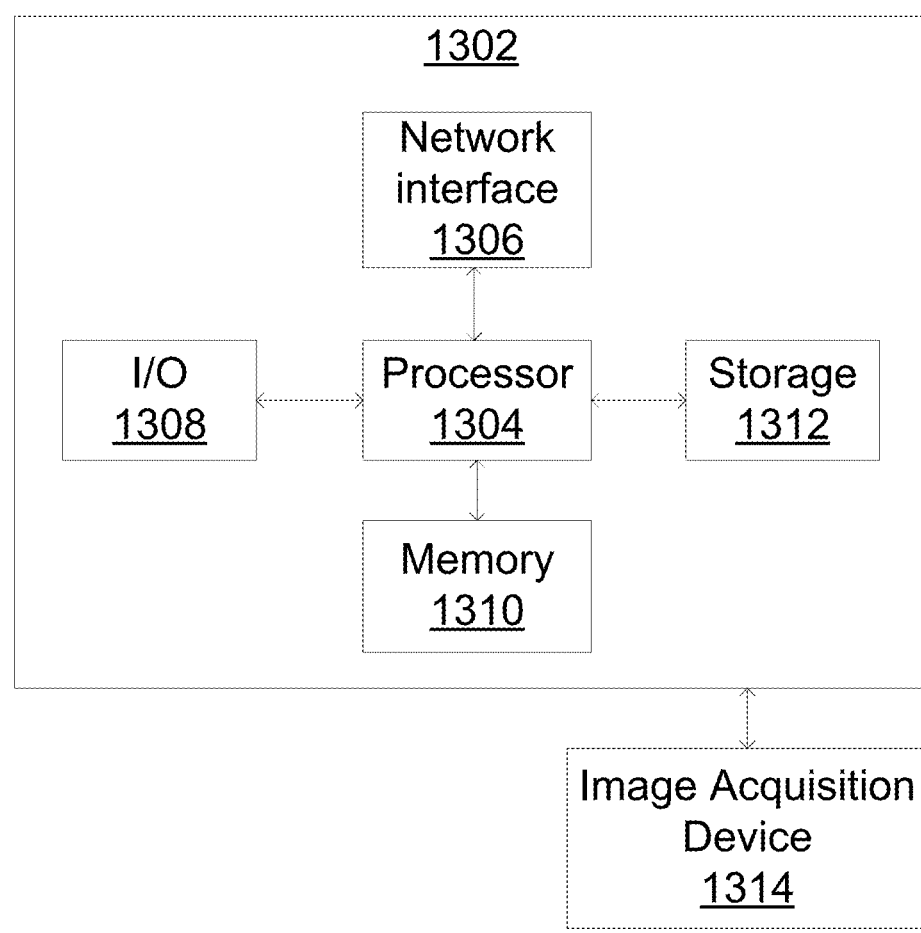
FIG. 13 shows a high-level block diagram of a computer that may be used to implement one or more embodiments.

A high-level block diagram of an example computer 1302 that may be used to implement systems, apparatus, and methods described herein is depicted in FIG. 13. Computer 1302 includes a processor 1304 operatively coupled to a data storage device 1312 and a memory 1310. Processor 1304 controls the overall operation of computer 1302 by executing computer program instructions that define such operations. The computer program instructions may be stored in data storage device 1312, or other computer readable medium, and loaded into memory 1310 when execution of the computer program instructions is desired. Thus, the method and workflow steps or functions of FIG. 3 can be defined by the computer program instructions stored in memory 1310 and/or data storage device 1312 and controlled by processor 1304 executing the computer program instructions. For example, the computer program instructions can be implemented as computer executable code programmed by one skilled in the art to perform the method and workflow steps or functions of FIG. 3. Accordingly, by executing the computer program instructions, the processor 1304 executes the method and workflow steps or functions of FIG. 3. Computer 1302 may also include one or more network interfaces 1306 for communicating with other devices via a network. Computer 1302 may also include one or more input/output devices 1308 that enable user interaction with computer 1302 (e.g., display, keyboard, mouse, speakers, buttons, etc.).

Processor 1304 may include both general and special purpose microprocessors, and may be the sole processor or one of multiple processors of computer 1302. Processor 1304 may include one or more central processing units (CPUs), for example. Processor 1304, data storage device 1312, and/or memory 1310 may include, be supplemented by, or incorporated in, one or more application-specific integrated circuits (ASICs) and/or one or more field programmable gate arrays (FPGAs).

Data storage device 1312 and memory 1310 each include a tangible non-transitory computer readable storage medium. Data storage device 1312, and memory 1310, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1308 may include peripherals, such as a printer, scanner, display screen, etc. For example, input/output devices 1308 may include a display device such as a cathode ray tube (CRT) or liquid crystal display (LCD) monitor for displaying information to the user, a keyboard, and a pointing device such as a mouse or a trackball by which the user can provide input to computer 1302.

An image acquisition device 1314 can be connected to the computer 1302 to input image data (e.g., medical images) to the computer 1302. It is possible to implement the image acquisition device 1314 and the computer 1302 as one device. It is also possible that the image acquisition device 1314 and the computer 1302 communicate wirelessly through a network. In a possible embodiment, the computer 1302 can be located remotely with respect to the image acquisition device 1314.

Any or all of the systems and apparatus discussed herein may be implemented using one or more computers such as computer 1302.

One skilled in the art will recognize that an implementation of an actual computer or computer system may have other structures and may contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving a plurality of partial point clouds of anatomical objects, each of the plurality of partial point clouds extracted from a respective one of a plurality of medical images;
generating a set of missing points for each of the plurality of partial point clouds;
determining a measure of certainty for each point in 1) the plurality of partial point clouds and 2) the sets of missing points;
determining one or more transformations aligning the plurality of partial point clouds based on the measures of certainty using a machine learning based point registration network for registering the plurality of medical images; and
outputting the one or more transformations.

2. The computer-implemented method of claim 1, wherein:
generating a set of missing points for each of the plurality of partial point clouds comprises generating the sets of missing points using a machine learning based point cloud completion network;
determining a measure of certainty for each point in 1) the plurality of partial point clouds and 2) the sets of missing points comprises determining the measures of certainty using a machine learning based point certainty estimation network; and
the machine learning based point cloud completion network, the machine learning based point certainty estimation network, and the machine learning based point registration network comprise a shared encoder.

3. The computer-implemented method of claim 2, wherein determining a measure of certainty for each point in 1) the plurality of partial point clouds and 2) the sets of missing points comprises, for each respective partial point cloud of the plurality of point clouds:
receiving, as input of a point certainty estimation decoder of the machine learning based point certainty estimation network, A) a set of features extracted from the respective partial point cloud via the shared encoder and B) the sets of missing points; and
generating as output the measure of certainty for each point in the respective partial point cloud and the sets of missing points based on the set of features and the sets of missing points.

4. The computer-implemented method of claim 2, wherein determining a measure of certainty for each point in 1) the plurality of partial point clouds and 2) the sets of missing points comprises, for each respective partial point cloud of the plurality of point clouds:
receiving, as input of a point certainty estimation decoder of the machine learning based point certainty estimation network, a set of features extracted from the respective partial point cloud via the shared encoder;
receiving, via conditional layers of the point certainty estimation decoder, the sets of missing points; and
generating as output the measure of certainty for each point in the respective partial point cloud and the sets of missing points based on the set of features and the sets of missing points.

5. The computer-implemented method of claim 2, wherein:
generating a set of missing points for each of the plurality of partial point clouds comprises transferring local shape features from the shared encoder to a point cloud completion decoder of the machine learning based point cloud completion network via at least one of skip connections or a feature pyramid.

6. The computer-implemented method of claim 2, wherein determining one or more transformations aligning the plurality of partial point clouds based on the measures of certainty using a machine learning based point registration network for registering the plurality of medical images comprises:
aggregating global and local shape features from the shared encoder with the measures of certainty; and
determining the one or more transformations based on the aggregated global and local shape features and the measures of certainty.

7. The computer-implemented method of claim 2, wherein the shared encoder is trained with at least one of self-supervised and contrastive learning methods in a generative adversarial network framework with adversarial learning.

8. The computer-implemented method of claim 2, wherein the machine learning based point cloud completion network is trained with adversarial learning using a multiscale discriminator, wherein the discriminator discriminates between a completed point cloud generated by the machine learning point cloud completion network and a ground truth completed point cloud.

9. The computer-implemented method of claim 1, wherein the machine learning based point registration network is trained with soft constraints and/or hard constraints based on prior knowledge on transformations and tissue properties.

10. An apparatus comprising:
means for receiving a plurality of partial point clouds of anatomical objects, each of the plurality of partial point clouds extracted from a respective one of a plurality of medical images;
means for generating a set of missing points for each of the plurality of partial point clouds;
means for determining a measure of certainty for each point in 1) the plurality of partial point clouds and 2) the sets of missing points;
means for determining one or more transformations aligning the plurality of partial point clouds based on the measures of certainty using a machine learning based point registration network for registering the plurality of medical images; and
means for outputting the one or more transformations.

11. The apparatus of claim 10, wherein:
the means for generating a set of missing points for each of the plurality of partial point clouds comprises means for generating the sets of missing points using a machine learning based point cloud completion network;
the means for determining a measure of certainty for each point in 1) the plurality of partial point clouds and 2) the sets of missing points comprises means for determining the measures of certainty using a machine learning based point certainty estimation network; and
the machine learning based point cloud completion network, the machine learning based point certainty estimation network, and the machine learning based point registration network comprise a shared encoder.

12. The apparatus of claim 11, wherein the means for determining a measure of certainty for each point in 1) the plurality of partial point clouds and 2) the sets of missing points comprises, for each respective partial point cloud of the plurality of point clouds:

means for receiving, as input of a point certainty estimation decoder of the machine learning based point certainty estimation network, A) a set of features extracted from the respective partial point cloud via the shared encoder and B) the sets of missing points; and means for generating as output the measure of certainty for each point in the respective partial point cloud and the sets of missing points based on the set of features and the sets of missing points.

13. The apparatus of claim 11, wherein the means for determining a measure of certainty for each point in 1) the plurality of partial point clouds and 2) the sets of missing points comprises, for each respective partial point cloud of the plurality of point clouds:

means for receiving, as input of a point certainty estimation decoder of the machine learning based point certainty estimation network, a set of features extracted from the respective partial point cloud via the shared encoder;

means for receiving, via conditional layers of the point certainty estimation decoder, the sets of missing points; and means for generating as output the measure of certainty for each point in the respective partial point cloud and the sets of missing points based on the set of features and the sets of missing points.

14. The apparatus of claim 11, wherein:

the means for generating a set of missing points for each of the plurality of partial point clouds comprises means for transferring local shape features from the shared encoder to a point cloud completion decoder of the machine learning based point cloud completion network via at least one of skip connections or a feature pyramid.

15. A non-transitory computer readable medium storing computer program instructions, the computer program instructions when executed by a processor cause the processor to perform operations comprising:

receiving a plurality of partial point clouds of anatomical objects, each of the plurality of partial point clouds extracted from a respective one of a plurality of medical images;

generating a set of missing points for each of the plurality of partial point clouds;

determining a measure of certainty for each point in 1) the plurality of partial point clouds and 2) the sets of missing points;

determining one or more transformations aligning the plurality of partial point clouds based on the measures of certainty using a machine learning based point registration network for registering the plurality of medical images; and outputting the one or more transformations.

16. The non-transitory computer readable medium of claim 15, wherein:

generating a set of missing points for each of the plurality of partial point clouds comprises generating the sets of missing points using a machine learning based point cloud completion network;

determining a measure of certainty for each point in 1) the plurality of partial point clouds and 2) the sets of missing points comprises determining the measures of certainty using a machine learning based point certainty estimation network; and the machine learning based point cloud completion network, the machine learning based point certainty estimation network, and the machine learning based point registration network comprise a shared encoder.

17. The non-transitory computer readable medium of claim 16, wherein determining one or more transformations aligning the plurality of partial point clouds based on the measures of certainty using a machine learning based point registration network for registering the plurality of medical images comprises:

aggregating global and local shape features from the shared encoder with the measures of certainty; and determining the one or more transformations based on the aggregated global and local shape features and the measures of certainty.

18. The non-transitory computer readable medium of claim 16, wherein the shared encoder is trained with at least one of self-supervised and contrastive learning methods in a generative adversarial network framework with adversarial learning.

19. The non-transitory computer readable medium of claim 16, wherein the machine learning based point cloud completion network is trained with adversarial learning using a multiscale discriminator, wherein the discriminator discriminates between a completed point cloud generated by the machine learning point cloud completion network and a ground truth completed point cloud.

20. The non-transitory computer readable medium of claim 15, wherein the machine learning based point registration network is trained with soft constraints and/or hard constraints based on prior knowledge on transformations and tissue properties.

* * * * *